(12) United States Patent
Cho

(10) Patent No.: US 8,129,137 B2
(45) Date of Patent: Mar. 6, 2012

(54) TWO-PHOTON PROBE FOR REAL-TIME MONITORING OF INTRACELLULAR FREE ZINC IONS, METHOD FOR PREPARING THE PROBE AND METHOD FOR REAL-TIME MONITORING OF INTRACELLULAR FREE ZINC IONS USING THE PROBE

(75) Inventor: Bong-Rae Cho, Seoul (KR)

(73) Assignee: Korea University Industrial & Academic Collaboration Foundation, Seoul (KR)

( * ) Notice: Subject to any disclaimer, the term of this patent is extended or adjusted under 35 U.S.C. 154(b) by 423 days.

(21) Appl. No.: 12/454,169

(22) Filed: May 12, 2009

(65) Prior Publication Data

US 2009/0286275 A1    Nov. 19, 2009

(30) Foreign Application Priority Data

May 13, 2008    (KR) .................. 10-2008-0044176

(51) Int. Cl.
  *C12Q 1/02* (2006.01)
  *C07D 213/00* (2006.01)
(52) U.S. Cl. ............... 435/29; 435/4; 435/325; 435/243
(58) Field of Classification Search ............... 435/4, 29, 435/325, 243; 546/329
  See application file for complete search history.

(56) References Cited

OTHER PUBLICATIONS

Kim et al. Angew. Chem. Int. Ed. (Jun. 27, 2008) published online Jun. 7, 2008 47: 5167-5170.*

Kim et al. Supporting Information for Kim et al. Angew. Chem. Int. Ed. (Jun. 27, 2008) published online Jun. 7, 2008 47: 5167-5170 from http://dx.doi.org/10.1002/anie.200800929 downloaded on Sep. 2, 2011, pp. S1-S21.*

Kim, H.M ,et al., *A Two-Photon Fluorescent Probe for Calcium Waves in Living Tissue*, Agnew Chem., (2007), vol. 46, pp. 7445-7448, International Edition.

Demas, et al., *J. Phys. Chem*. 1971, 75, pp. 991-1024.

* cited by examiner

*Primary Examiner* — Susan Hanley
(74) *Attorney, Agent, or Firm* — Christie, Parker & Hale, LLP

(57) ABSTRACT

A two-photon probe for real-time monitoring of intracellular free zinc ions is provided. The two-photon probe is represented by Formula 1:

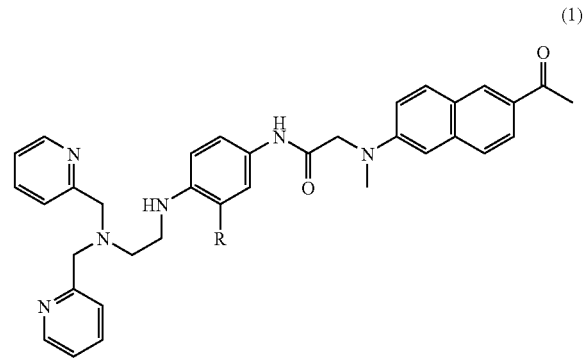

(1)

wherein R is H or $OCH_3$. The two-photon probe has high selectivity for $Zn^{2+}$ and enables very effective and long-term monitoring of intracellular free $Zn^{2+}$ present in the deep tissue. Further provided are a method for preparing the two-photon probe and a method for real-time monitoring of intracellular free zinc ions using the two-photon probe.

8 Claims, 17 Drawing Sheets

(9 of 17 Drawing Sheet(s) Filed in Color)

~ 3.0 μM

TWO-PHOTON PROBE FOR REAL-TIME MONITORING OF INTRACELLULAR FREE ZINC IONS, METHOD FOR PREPARING THE PROBE AND METHOD FOR REAL-TIME MONITORING OF INTRACELLULAR FREE ZINC IONS USING THE PROBE

CROSS-REFERENCE TO RELATED APPLICATIONS

This application claims priority to and the benefit of Korean Patent Application No. 10-2008-0044176, filed on May 13, 2008, in the Korean Intellectual Property Office.

BACKGROUND OF THE INVENTION

1. Field of the Invention

The present invention relates to a two-photon probe for real-time monitoring of intracellular free zinc ions, a method for preparing the two-photon probe, and a method for real-time monitoring of intracellular free zinc ions using the two-photon probe. More specifically, the two-photon probe has the ability to detect zinc ions deep inside live cells for a long period of time, thus being suitable for real-time imaging of intracellular free zinc ions.

2. Description of the Related Art

Zinc is a vital component of enzymes and proteins. In the brain, a few millimoles of intracellular free $Zn^{2+}$ is stored in the presynaptic vesicles, released with synaptic activation, and seems to modulate excitatory neurotransmission. To understand the biological roles of zinc, a variety of fluorescent probes derived from quinoline (TSQ, Zinquin, and TFLZn) and fluoroscein (FluZn-3, Znpyr, ZnAF, etc.) have been developed.

However, most of such fluorescent probes require rather short excitation wavelength or suffer from pH sensitivity. To visualize the biological activity deep inside the live tissue (>80 μm) without the interference of surface preparation artifacts, two-photon microscopy (TPM) utilizing two-photons with low excitation energy is very effective. In particular, TPM employing two near-infrared photons for the excitation offers a number of advantages, including increased penetration depth, localized excitation and prolonged observation time, over one-photon microscopy (OPM). However, two-photon probes having the above advantages and being capable of effectively monitoring intracellular zinc ions appear to be rare. Although a few pH-resistant sensors for $Zn^{2+}$ have been reported, they require either microinjection for cellular applications or use significant amount of ethanol as the co-solvent due to the poor water solubility.

There has been no efficient two-photon probe for $Zn^{2+}$ that satisfies all requirements, including sufficient water solubility to stain cells, high selectivity for $Zn^{2+}$, significant two-photon cross section, pH-resistance, and high photostability, and can monitor intracellular free zinc ions.

SUMMARY OF THE INVENTION

A first object of the present invention is to provide a two-photon probe for monitoring free zinc ions in live cells and tissues, particularly intracellular free zinc ions, in a more effective and selective manner.

A second object of the present invention is to provide a method for preparing the two-photon probe.

A third object of the present invention is to provide a method for real-time monitoring of intracellular free zinc ions using the two-photon probe.

According to an aspect of the present invention, there is provided a two-photon probe for real-time monitoring of intracellular free zinc ions, represented by Formula 1:

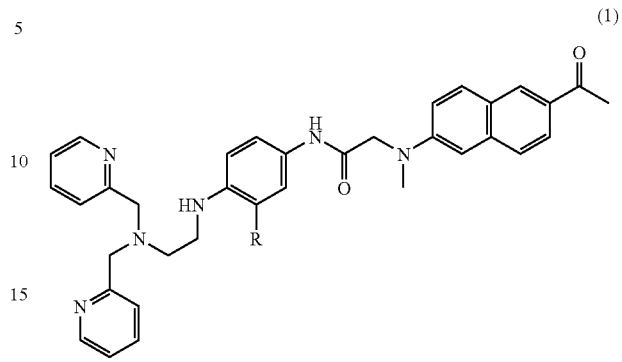

(1)

wherein R is H or $OCH_3$.

According to another aspect of the present invention, there is provided a method for preparing a two-photon probe for real-time monitoring of intracellular free zinc ions, represented by Formula 1:

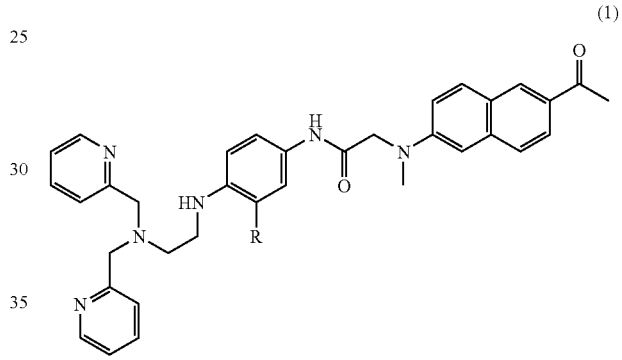

(1)

wherein R is H or $OCH_3$, the method including (a) adding the compound of Formula 2:

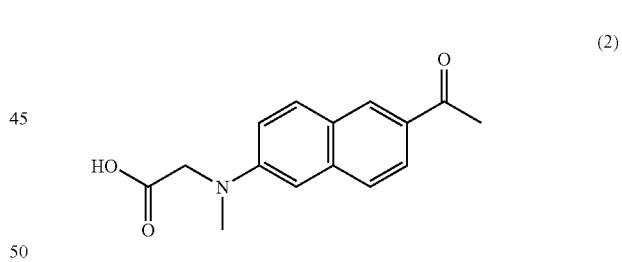

(2)

to an organic solvent and stirring the mixture, and (b) reacting the compound of Formula 2 with the compound of Formula 3:

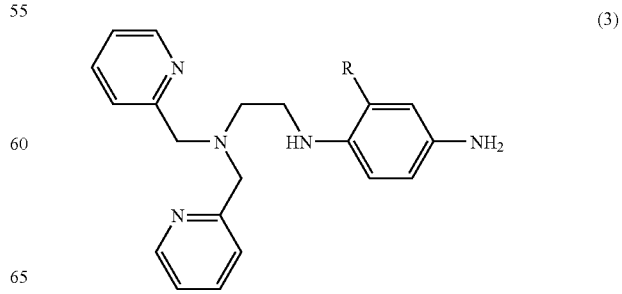

(3)

The method of the present invention may further include isolating the compound of Formula 1 from the reaction product after step (b). In an embodiment, the compound of Formula 1 may be isolated by extraction. In an embodiment, the organic solvent may be 1-hydroxybenzotriazole or 1,3-dicyclohexylcarbodiimide.

According to yet another aspect of the present invention, there is provided a method for real-time monitoring of intracellular free zinc ions, the method including injecting the two-photon probe of Formula 1 into cells of interest and observing two-photon excitation fluorescence (TPEF) images of the cells. The TPEF images may be those obtained from the cells at a depth of 80 to 150 μm. The TPEF images may be observed for longer than 1,000 seconds.

BRIEF DESCRIPTION OF THE DRAWINGS

The patent or application file contains at least one drawing executed in color. Copies of this patent or application publication with color drawing(s) will be provided by the Office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Figure 1A:
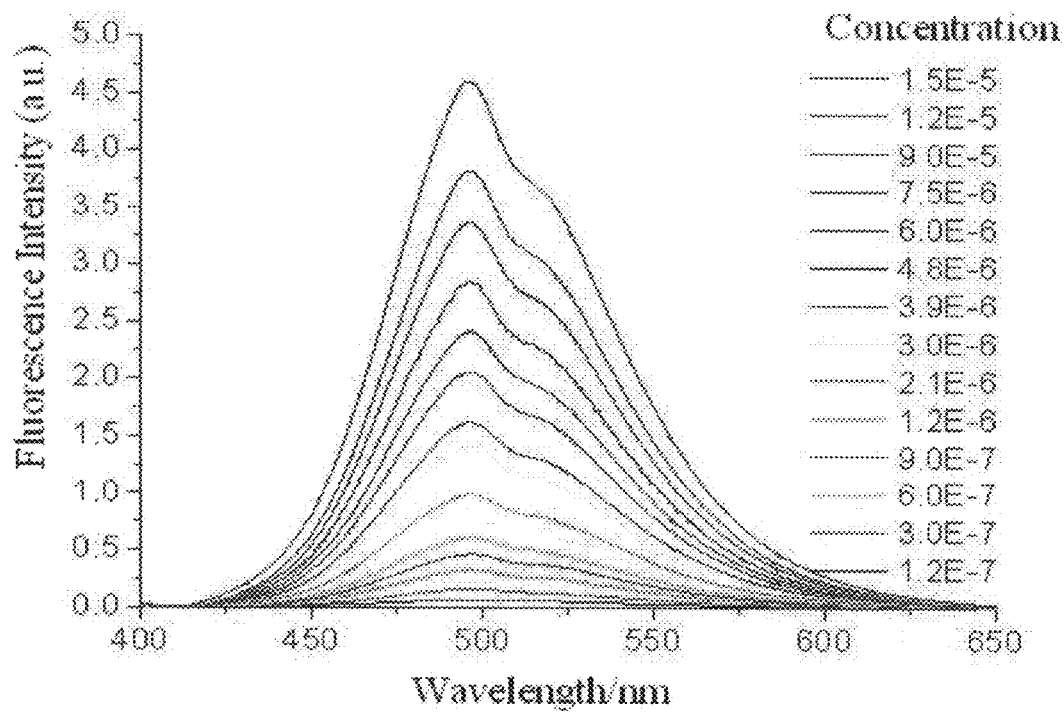
FIGS. 1a through 1d are plots showing variations in the fluorescence intensity of a two-photon probe (AZn2) prepared in Example 1 and a two-photon probe (AZn1) prepared in Example 2 at different concentrations.

The present invention provides a two-photon probe for monitoring intracellular free zinc ions, represented by Formula 1:

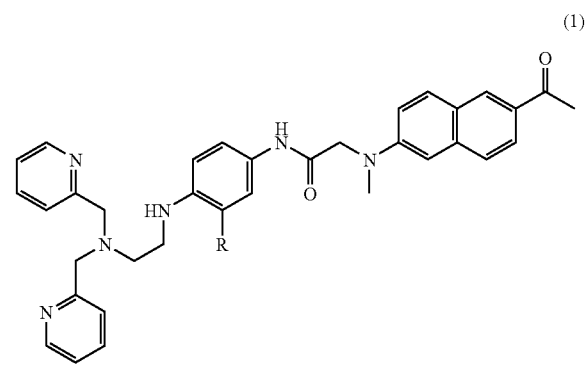

(1)

wherein R is H or $OCH_3$.

The two-photon probe of the present invention has a structure in which 2-acetyl-6-(dimethylamino)naphthalene (acedan) as a fluorophore is bonded to a N,N-di-(2-picolyl) ethylenediamine (DPEN) derivative as a $Zn^{2+}$ chelator. The two-photon probe of the present invention is capable of imaging the intracellular free $Zn^{2+}$ in live cells for a long period of time and living tissue at >80 μm depth without mistargeting and photobleaching problems.

Hereinafter, the present invention will be explained in detail with reference to the following examples.

Several two-photon probes capable of monitoring intracellular free $Zn^{2+}$ were prepared in Examples 1 and 2, and their excellent characteristics were evaluated in Experimental Examples 1-11.

EXAMPLES

Example 1

Synthesis of N-(4-(2-(bis(pyridin-2-yl)methyl) amino)ethylamino)-3-methoxyphenyl)-2-(N-(2-acetylnaphthalen-6-yl)-N-methylamino)acetamide 1-1. Synthesis of N-(2-methoxy-4-nitrophenyl)ethylenediamine 2-Chloro-5-nitroanisole (3.0 g, 16.0 mmol) and ethylenediamine (7.7 g, 8.6 ml, 0.13 mol) were added to water (180 ml). The mixture was stirred at 110° C. for 72 hours. The reaction mixture was extracted with ethyl acetate, dried over $MgSO_4$, filtered and concentrated under vacuum. The crude product was purified by flash column chromatography using chloroform/methanol (5:1) as the eluent and recrystallized from ethanol to give the compound of Formula 4:

(4)

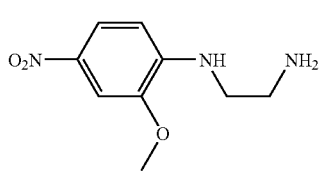

Yield: 2.0 g (60%); mp 183° C.; IR (KBr): 3,440, 2,960, 2,890 cm$^{-1}$; $^1$H NMR (400 MHz, CDCl$_3$): δ 7.91 (dd, 1H, J=8.9, J=2.1 Hz), 7.63 (d, 1H, J=2.1 Hz, 6.52 (d, 1H, J=8.9 Hz), 5.41 (br s, 1H), 3.94 (s, 3H), 3.31 (t, 2H, J=5.4 Hz), 3.03 (t, 2H, J=5.4 Hz); $^{13}$C NMR (100 MHz, CDCl$_3$): δ 171.8, 145.4, 144.4, 120.1, 106.6, 104.9, 56.2, 43.4, 39.1 ppm; Anal. Calcd. for C$_9$H$_{13}$N$_3$O$_3$: C, 51.73; H, 6.51; N, 19.44. Found: C, 51.38; H, 6.20; N, 19.29.

1-2. Synthesis of N-(2-methoxy-4-nitrophenyl)-N',N'-[bis(2-pyridylmethyl)]ethylenediamine The compound prepared in 1-1, 2-(chloromethyl)pyridine hydrochloride (2.9 g, 17.5 mmol), KI (0.52 g, 3.0 mmol) and N,N-diisopropylethylamine (20 g, 27 ml, 0.16 mol) were added to acetonitrile (50 ml). The mixture was refluxed under a nitrogen atmosphere for 16 hours. The reaction mixture was extracted with ethyl acetate, dried over MgSO$_4$, filtered and concentrated under vacuum. The crude product was purified by flash column chromatography using chloroform/methanol (4:1~1:1) as the eluent to give the compound of Formula 5:

(5)

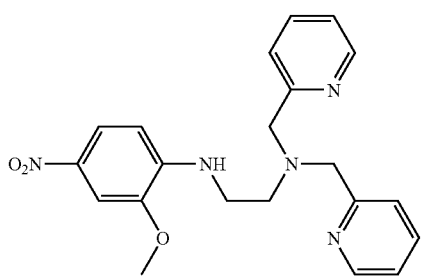

Yield: 2.2 g (90%); IR (KBr): 3,428 cm$^{-1}$; $^1$H NMR (400 MHz, CDCl$_3$): δ 8.55 (dd, 2H, J=5.0, J=2.0 Hz), 7.85 (dd, 1H, J=9.0, J=2.0 Hz), 7.64 (td, 2H, J=7.5, 2.0 Hz), 7.62 (d, 1H, J=2.0 Hz), 7.44 (dd, 2H, J=7.5, 1.0 Hz), 7.17 (ddd, 2H, J=7.5, 5.0, 1.0 Hz), 6.36 (d, 1H, J=9.0 Hz), 6.10 (br s, 1H), 3.99 (s, 3H), 3.92 (s, 4H), 3.29 (t, 2H, J=5.4 Hz), 2.93 (t, 2H, J=5.4 Hz); $^{13}$C NMR (100 MHz, CDCl$_3$): δ 170.5, 159.0, 149.2, 145.5, 144.5, 137.0, 123.7, 122.6, 120.1, 106.7, 104.9, 60.1, 52.9, 37.6, 23.3 ppm; Anal. Calcd. for C$_{21}$H$_{23}$N$_5$O$_3$: C, 64.28; H, 5.99; N, 17.24. Found: C, 64.11; H, 5.89; N, 17.80

1-3. Synthesis of N-(4-amino-2-methoxyphenyl)-N', N'-[bis(2-pyridylmethyl)]ethylenediamine A mixture of the compound (1.2 g, 3.00 mmol) prepared in 1-2 and SnCl$_2$.H$_2$O (7.4 g, 33 mmol) was refluxed in acetonitrile (50 ml) and absolute ethanol (40 ml) for 12 hours. The reaction mixture was neutralized with saturated sodium carbonate (100 ml) and extracted with dichloromethane. The crude product was purified by flash column chromatography using chloroform/methanol (20:3) as the eluent to give the compound of Formula 6:

(6)

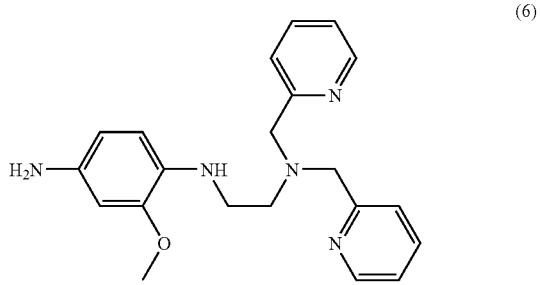

Yield: 0.9 g (80%); IR (KBr): 3,419 cm$^{-1}$; $^1$H NMR (400 MHz, CDCl$_3$): δ 8.50 (dd, 2H, J=J=5.0, J=2.0 Hz), 7.63 (td, 2H, J=7.5, 2.0 Hz), 7.53 (dd, 2H, J=7.5, 1.0 Hz), 7.13 (ddd, 2H, J=7.5, 5.0, 1.0 Hz), 6.39 (d, 1H, J=9.0 Hz), 6.27 (d, 1H, J=2.0 Hz), 6.22 (dd, 1H, J=9.0, J=2.0 Hz), 3.86 (s, 4H), 3.84 (s, 3H), 3.15 (t, 2H, J=5.4 Hz), 2.88 (t, 2H, J=5.4 Hz); $^{13}$C NMR (100 MHz, CDCl$_3$): δ 159.6, 149.1, 148.4, 137.6, 136.7, 131.2, 123.2, 122.3, 112.0, 107.9, 100.1, 60.5, 55.7, 53.4, 42.3 ppm; Anal. Calcd. for C$_{21}$H$_{25}$N$_5$O: C, 69.55; H, 6.89; N, 18.98. Found: C, 69.40; H, 6.93; N, 19.27.

1-4. Synthesis of Two-Photon Probe (AZn2) for Monitoring Free Zn$^{2+}$ Ions

6-Acyl-2-[N-methyl-N-(carboxymethyl)amino]naphthalene (0.07 g, 0.27 mmol), 1-hydroxybenzotriazole (0.037 g, 0.27 mmol) and 1,3-dicyclohexylcarbodiimide (0.057 g, 0.28 mmol) were added to dichloromethane. After stirring for 30 minutes, the compound of Formula 6 prepared in 1-3 was added thereto. The resulting mixture was stirred under a nitrogen atmosphere for 12 hours. The reaction mixture was extracted with dichloromethane, dried over MgSO$_4$, and evaporated under vacuum to remove the solvent. The crude product was purified by flash column chromatography using chloroform/methanol (20:1) as the eluent to give the two-photon probe for monitoring free Zn$^{2+}$ ions, represented by Formula 7:

(7)

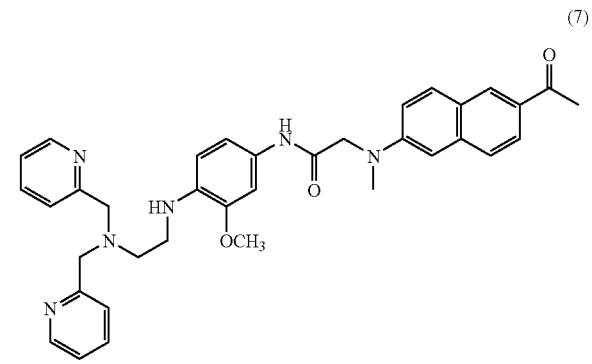

Example 2

Synthesis of Two-Photon Probe (AZn1) for Monitoring Free $Zn^{2+}$ Ions

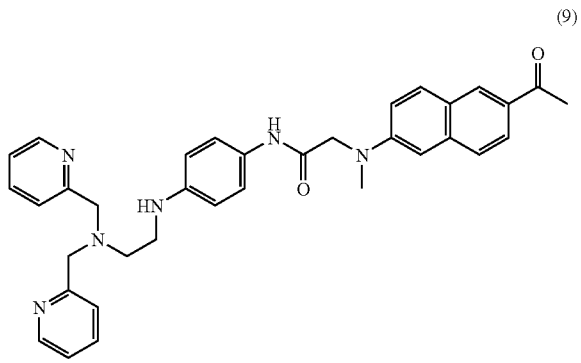

(9)

The two-photon probe of Formula 9 was synthesized in the same manner as in Example 1 except that the compound of Formula 8 was used instead of the compound of Formula 6.

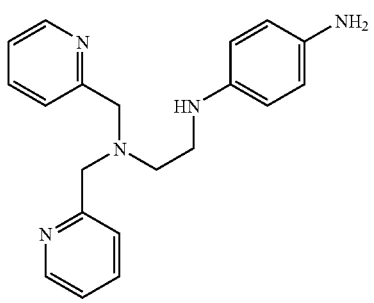

(8)

Experimental Example 1

Measurement of Water Solubility

A small amount of each of the two-photon probes (AZn2 and AZn1) prepared in Examples 1 and 2 was dissolved in DMSO to prepare a stock solution ($1.0 \times 10^{-3}$ M). The solution was diluted to $6.0 \times 10^{-3} \sim 6.0 \times 10^{-5}$ M and added to a cuvette containing 3.0 mL of $H_2O$ by using a micro syringe. In all cases, the concentration of DMSO in $H_2O$ was maintained to be 0.2%.

FIGS. 1a through 1d are plots showing variations in the fluorescence intensity of the two-photon probes at different concentrations.

Figure 1B:
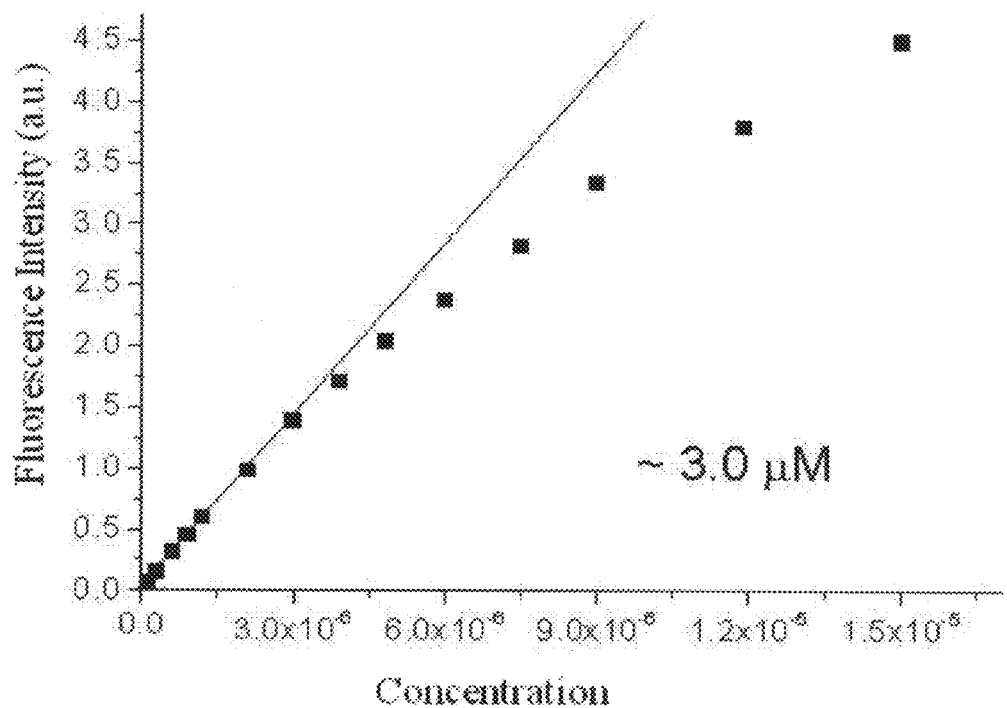
Figure 1C:
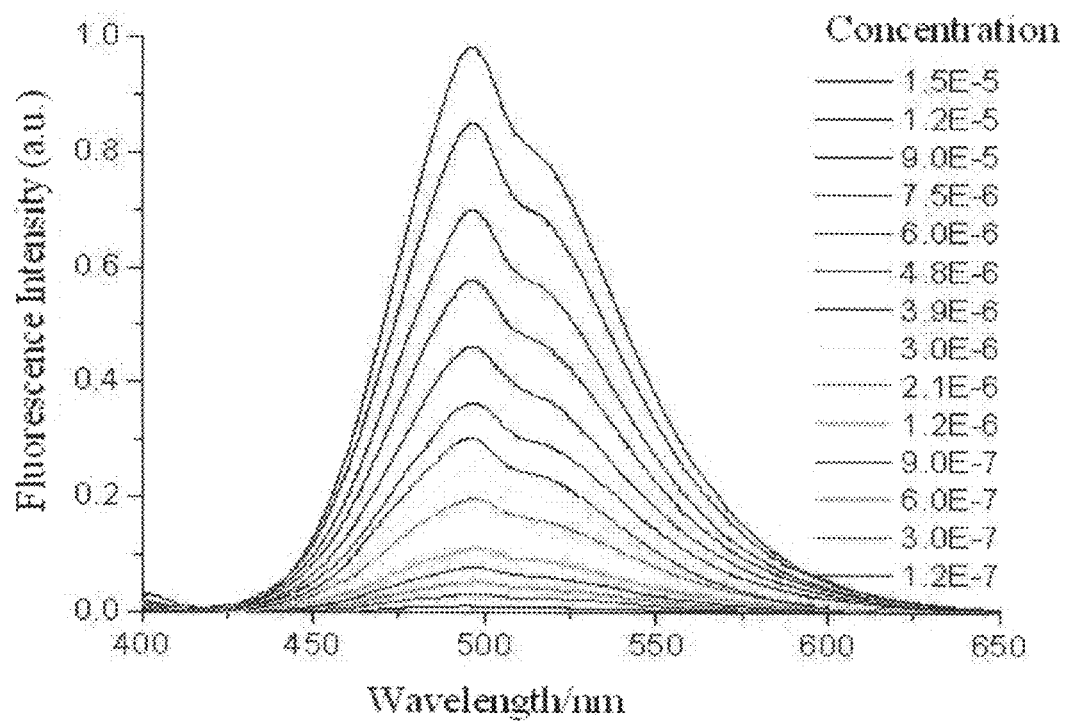
Figure 1D:
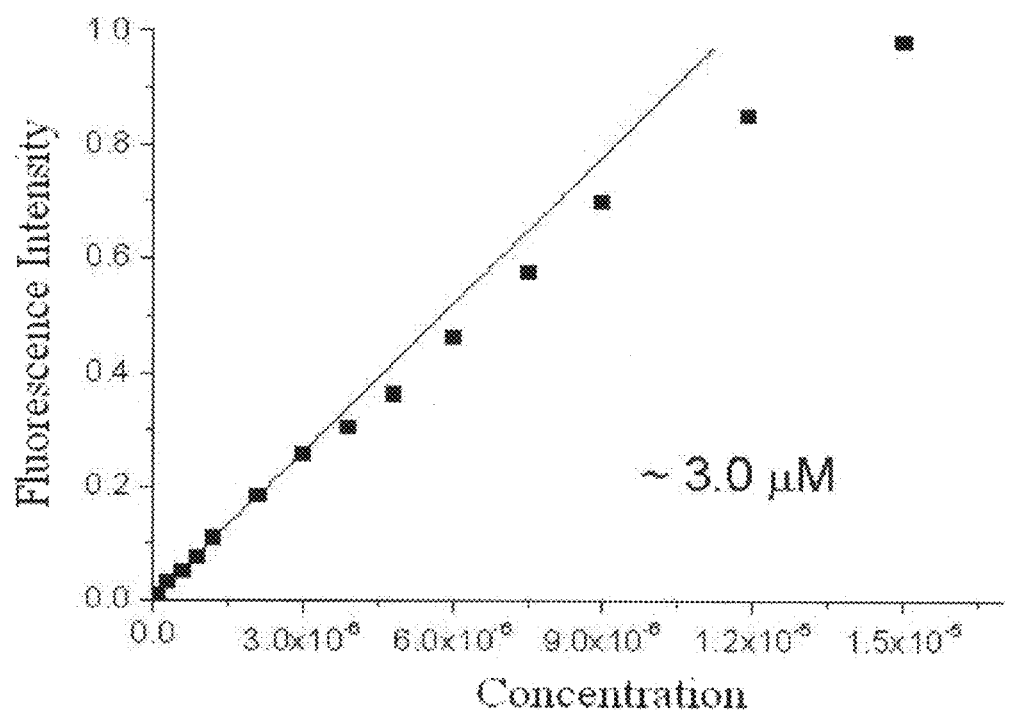

The plots of FIGS. 1b and 1d show variations in the fluorescence intensity of AZn2 and AZn1 as a function of the probe concentration, respectively, and have a profile in which the fluorescence intensity increases linearly at low concentrations. Thereafter, the profile shows a downward curvature with increasing probe concentration. The maximum concentration in the linear region was taken as the water solubility. The water solubilities of the two probes were all 3.0 μM. These results indicate that the probes are very effective in staining cells.

Experimental Example 2

Measurement of Absorption and Emission Spectra

Figure 2A:
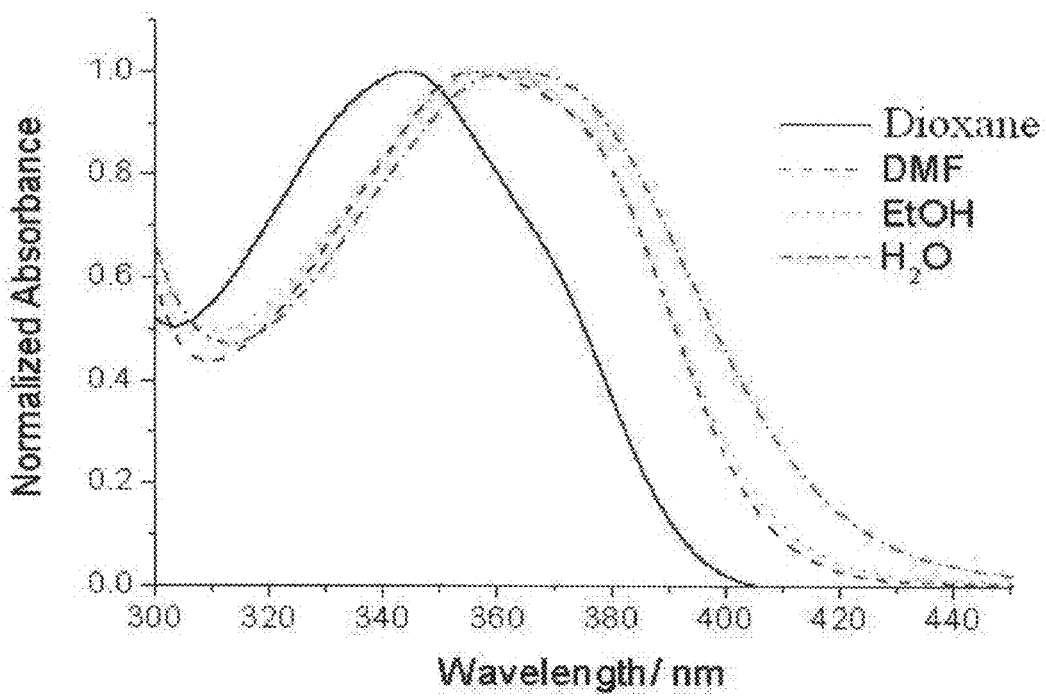
FIGS. 2a and 2b are one-photon absorption and emission spectra of AZn1, respectively.
Figure 2B:
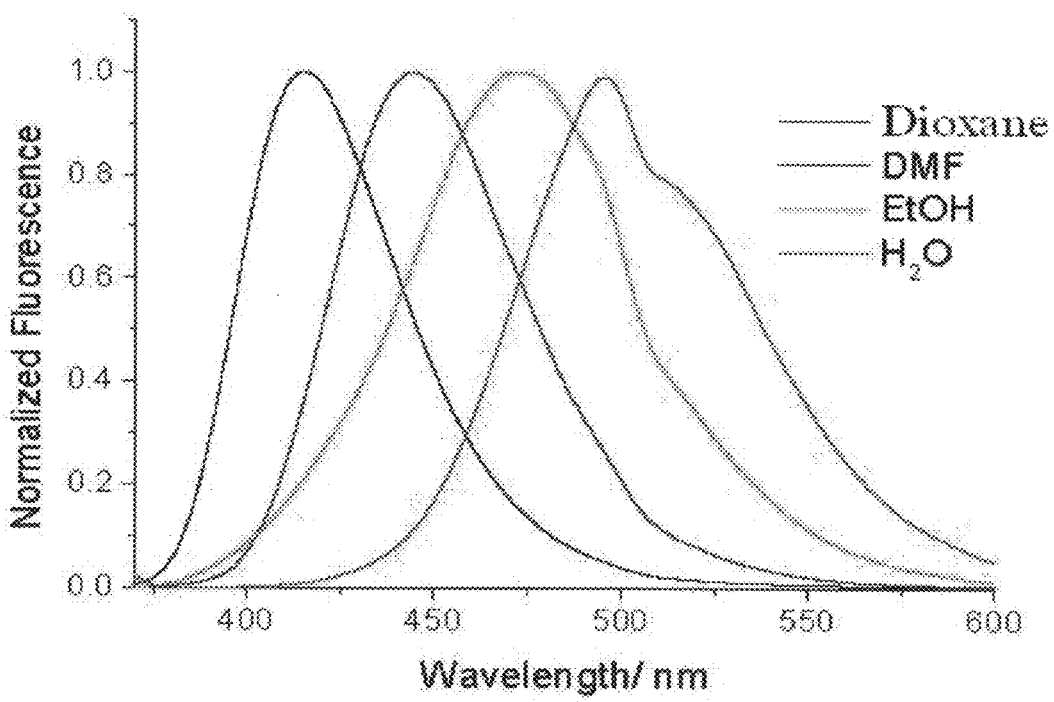
Figure 2C:
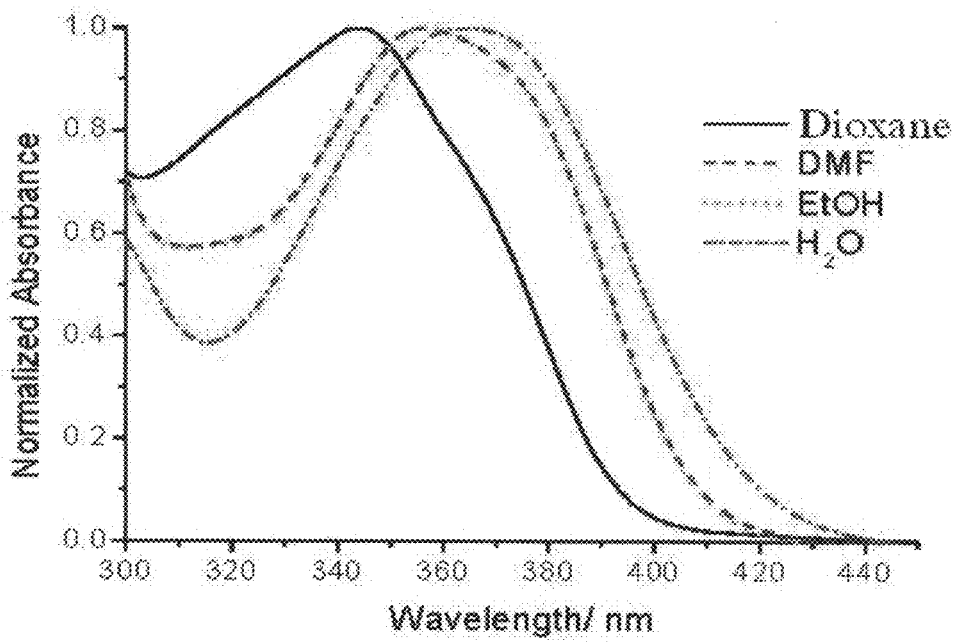
FIGS. 2c and 2d are one-photon absorption and emission spectra of AZn2, respectively.
Figure 2D:
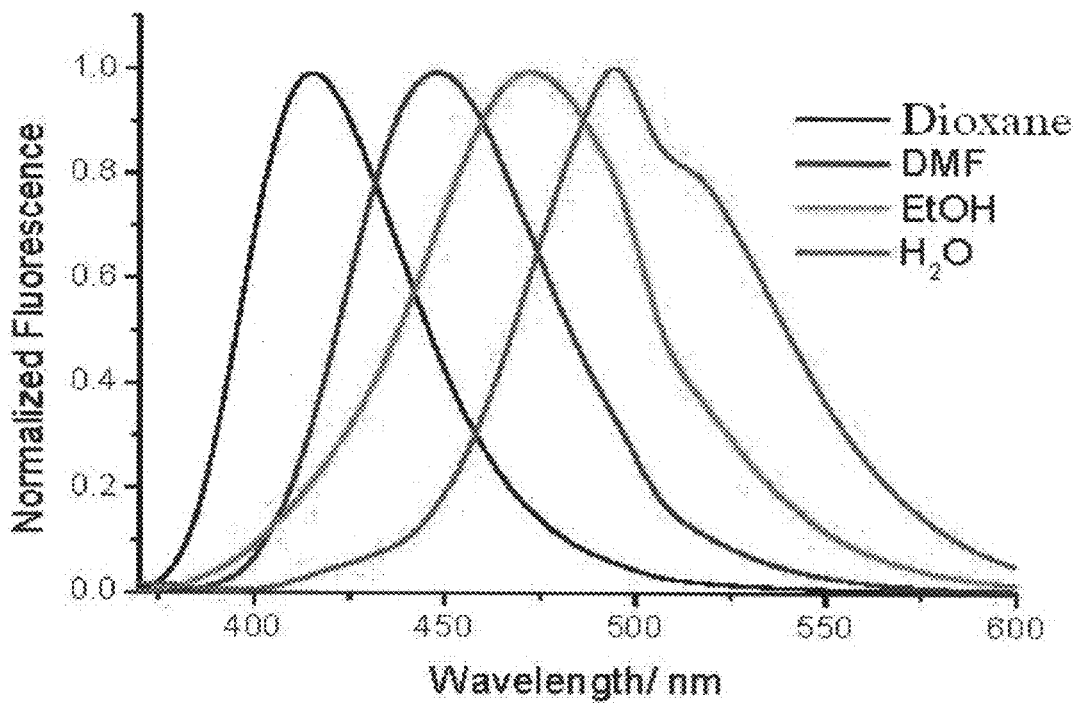

The absorption spectra of the two-photon probes were recorded on a Hewlett-Packard 8453 diode array spectrophotometer, and the fluorescence spectra of the two-photon probes were obtained with an Amico-Bowman series 2 luminescence spectrometer with a 1 cm standard quartz cell. The fluorescence quantum yields of the two-photon probes were determined by using Coumarin 307 as the reference by the literature method (J. N. Demas, G. A. Crosby, *J. Phys. Chem.* 1971, 75, 991-1024.). FIGS. 2a and 2b are one-photon absorption and emission spectra of the two-photon probe AZn1, respectively, and FIGS. 2c and 2d are one-photon absorption and emission spectra of the two-photon probe AZn2, respectively.

Table 1 shows the absorption ($\lambda_{max}^{(1)}$) and emission maxima ($\lambda_{max}^{fl}$) and fluorescence quantum yields ($\phi$) of the two-photon probes AZn1 and AZn2 in various solvents.

TABLE 1

| | $\lambda_{max}^{(1)}$ | | $\lambda_{max}^{fl}$ | | $\phi$ | |
|---|---|---|---|---|---|---|
| Solvent ($E_T^N$) | AZn1 | AZn2 | AZn1 | AZn2 | AZn1 | AZn2 |
| 1,4-dioxane (0.164) | 344 | 344 | 414 | 415 | 0.19 | 0.094 |
| DMF (0.386) | 356 | 356 | 442 | 448 | 0.055 | 0.037 |
| Ethanol (0.654) | 359 | 356 | 475 | 472 | 0.057 | 0.039 |
| $H_2O$ (1.000) | 363 | 366 | 496 | 495 | 0.022 | 0.012 |

*: The numbers in the parenthesis are normalized empirical parameters of solvent polarity.
$\lambda_{max}$ is expressed in nm.
Fluorescence quantum yield ±15%.

The spectra of FIGS. 2a through 2d and the results in Table 1 show large bathochromic shifts with the solvent polarity in the order, 1,4-dioxane<DMF<EtOH<$H_2O$, thus indicating the utility of the two-photon probes as polarity probes.

Experimental Example 3

Measurement of Absorbance with Varying $Zn^{2+}$ Concentrations

The one-photon absorption and emission spectra and two-photon emission spectra of the two-photon probes AZn2 and AZn1 were measured with varying $Zn^{2+}$ concentrations, and the results are shown in FIGS. 3a through 3f.

As can be known from FIGS. 3a through 3f, when small increments of $Zn^{2+}$ were added to AZn1 and AZn2 in MOPS buffer solution (30 mM, pH 7.2, /=0.10), the one- and two-photon excitation fluorescence (emission) intensity increased gradually without affecting the absorption spectra, presumably due to the blocking of the photo-induced electron transfer (PET) process by the complexation with $Zn^{2+}$.

Experimental Example 4

Comparison of Two-Photon Spectra of the Two-Photon Probes and Commercial Probes The fluorescence enhancement factors [FEF=(F-$F_{min}$)/$F_{min}$] of the two-photon probe AZn2 measured for one- and two-photon processes were 2.5-fold larger than those of the two-photon probe AZn1 as a result of the lower fluorescence quantum yield ($\Phi$) in the absence, and higher $\Phi$ in the presence, of excess $Zn^{2+}$. These analytical results can be more easily understood from the data in Table 2.

TABLE 2

| Compound[a] | $\lambda_{max}^{(1)[b]}$ | $\lambda_{max}^{fl[b]}$ | $\phi^{[c]}$ | $K_d^{OP}/K_d^{TP[d]}$ | $FEF^{OP}/FEF^{TP[e]}$ | $\lambda_{max}^{(2)[f]}$ | $\delta^{[g]}$ | $\phi\delta^{[h]}$ |
|---|---|---|---|---|---|---|---|---|
| AZn1 | 365 | 496 | 0.022 | — | — | nd[i] | nd[i] | nd[i] |
| AZn1 + Zn$^{2+}$ | 365 | 498 | 0.47 | 1.1/1.1 | 21/24 | 780 | 210 | 86 |
| AZn2 | 365 | 494 | 0.012 | — | — | nd[i] | nd[i] | nd[i] |
| AZn2 + Zn$^{2+}$ | 365 | 499 | 0.65 | 0.5/0.5 | 54/52 | 780 | 140 | 95 |
| FluZin + Zn$^{2+}$ | 494[j] | 516[j] | 0.43[j] | 15[j]/— | 50[j]/— | 780 | 55 | 24 |
| TSQ + Zn$^{2+[k]}$ | 362 | 495 | 0.43 | — | — | 780 | 10 | 4 |

[a]All data were measured in 20 mM MOPS, 100 mM KCl, 10 mM EGTA and pH 7.2 in the absence and presence of Zn$^{2+}$.
[b]$\lambda_{max}$ of the one-photon absorption and emission spectra in nm.
[c]Fluorescence quantum yield, ±10%.
[d]Dissociation constants for Zn$^{2+}$ measured by one-($K_d^{OP}$) and two-photon ($K_d^{TP}$) processes.
[e]Fluorescence enhancement factor measured by one-(FEF$^{OP}$) and two-photon (FEF$^{TP}$) processes.
[f]$\lambda_{max}^{(2)}$ of the two-photon excitation spectra in nm.
[g]The peak two-photon cross section in 10$^{-5}$ cm$^4$s/photon.
[h]Two-photon action cross section.
[i]The two-photon excited fluorescence intensity was too weak to measure the cross section accurately.
[k]The results were obtained in methanol in the presence of Zn$^{2+}$.

Experimental Example 5

Computational Analysis

The geometries of N,N-di-2-picolylethylenediamine (DPEN, R1), 2-methoxy-DPEN (R2), AZn1, AZn2 and AZn1–Zn$^{2+}$ and AZn2–Zn$^{2+}$ complexes were optimized at the density functional theory (DFT)-B3LYP/6-31G level using Gaussian 0.3 program. The calculated HOMO and LUMO energies are shown in Table 3.

TABLE 3

|  | HOMO (eV) | LUMO (eV) | Total energy (hartree) |
|---|---|---|---|
| R1 | −4.948 | −0.688 | −1202.418503 |
| R2 | −4.246 | −0.747 | −1316.936545 |
| AZn1 | −4.535 | −1.589 | −1834.429445 |
| AZn2 | −4.340 | −1.648 | −1948.949859 |
| AZn1 – Zn$^{2+}$ | −8.762 | −7.329 | −3689.630523 |
| AZn2 – Zn$^{2+}$ | −8.733 | −7.196 | −3804.163346 |

As shown in Table 3, in all cases, the CH$_3$O group increases the HOMO energy levels. This tendency diminishes as the molecular structure becomes more complex, i.e. in the order of R>AZn>AZn–Zn$^{2+}$. This means that the electron transfer from the HOMO of R2 to AZn2 emits a larger energy (i.e. heat) than the electron transfer from R1 to AZn1 (exothermic reaction). Table 3 also shows that the HOMO energies of R1, R2, AZn1, and AZn2 are −4.948, −4.246, −8.762, and −8.733 eV, respectively. This reveals that the PET from R2 to AZn2 might occur more efficiently on thermodynamic ground, thereby decreasing the Φ. On the other hand, the larger Φ for AZn2–Zn$^{2+}$ (see Table 2) may be attributed to the tighter binding, which may reduce the vibrational relaxation pathways.

Figure 4A:
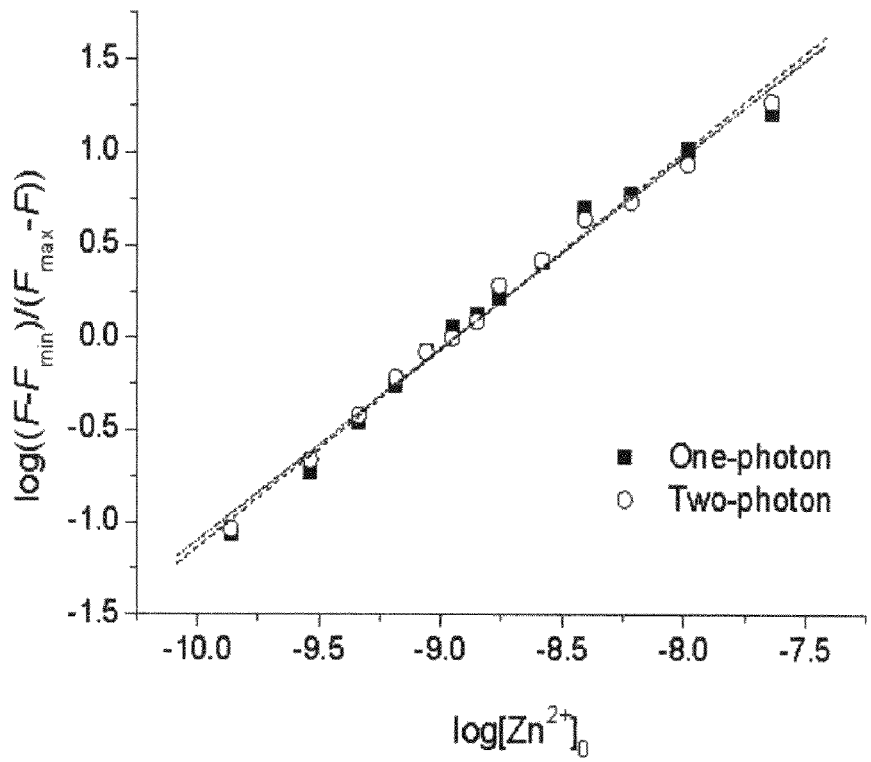
FIGS. 4a and 4b are Hill plots for the complexation of AZn1 and AZn2 with free $Zn^{2+}$.
Figure 4B:
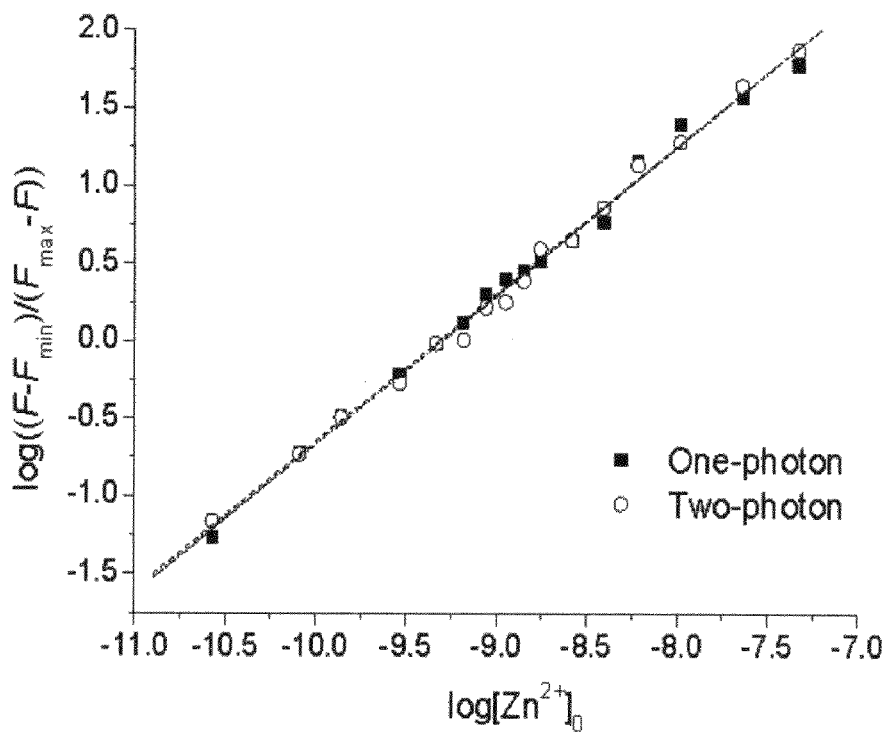

FIGS. 4a and 4b are Hill plots for the complexation of AZn1 and AZn2 with free Zn$^{2+}$ respectively.

Referring to FIGS. 4a and 4b, the linear Hill plots with a slope of 1.0 indicated 1:1 complexation between the two-photon probes and Zn$^{2+}$.

Figure 5:
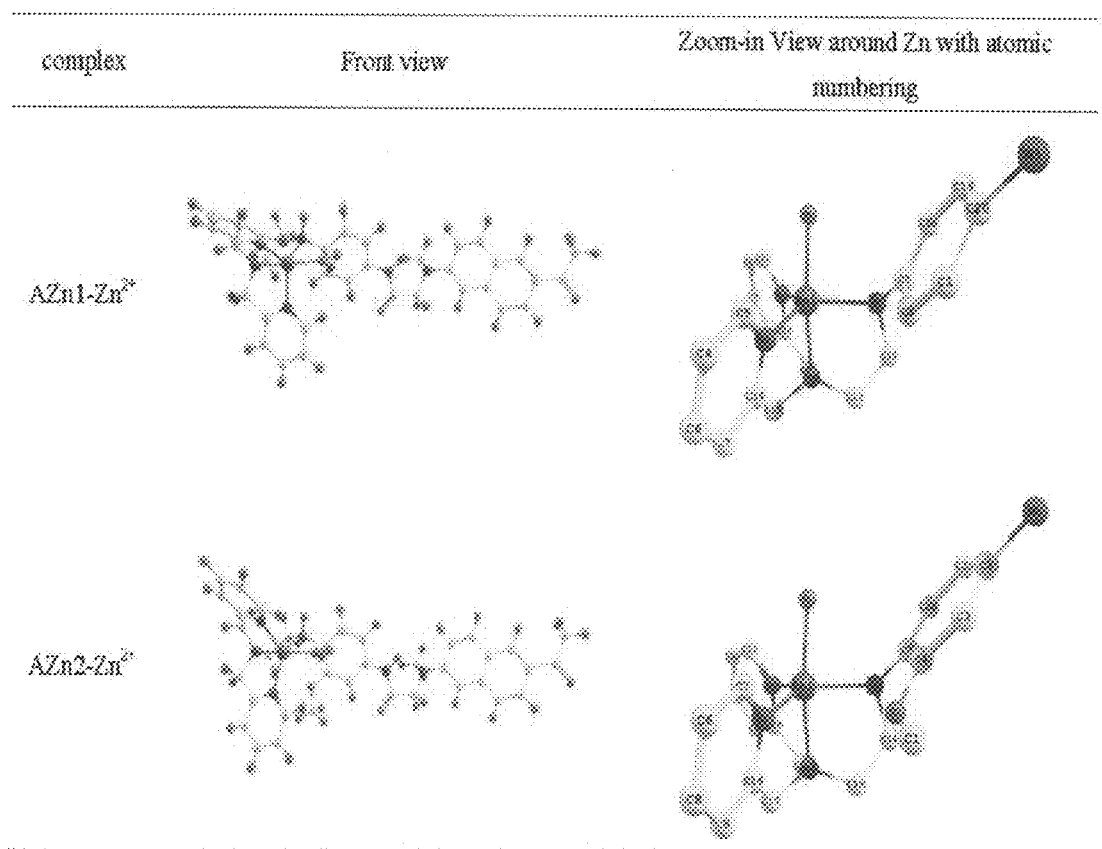
FIG. 5 shows three-dimensional views illustrating the optimized geometries of AZn1–$Zn^{2+}$ and AZn2–$Zn^{2+}$ complexes at the B3LYP/6-31G* level.

Furthermore, the optimized geometries of the AZn1–Zn$^{2+}$ and AZn2–Zn$^{2+}$complexes are trigonal bipyramidal in which Zn$^{2+}$ ions are coordinated by four nitrogen atoms and one water molecule. This can also be understood by FIG. 5 illustrating the optimized geometries of the AZn1–Zn$^{2+}$ and AZn2–Zn$^{2+}$ complexes at the B3LYP/6-31G* level.

The bond lengths and angles in the AZn1–Zn$^{2+}$ and AZn2–Zn$^{2+}$ complexes were calculated at the B3LYP/6-31 G** level, and the results are shown in Table 4.

TABLE 4

|  | AZn1 – Zn$^{2+}$ | AZn2 – Zn$^{2+}$ |
|---|---|---|
| r(Zn – N$_1$) | 2.098 | 2.099 |
| r(Zn – N$_2$) | 2.040 | 2.033 |
| r(Zn – N$_3$) | 2.045 | 2.060 |
| r(Zn – N$_4$) | 2.169 | 2.158 |
| r(Zn – O$_1$) | 2.143 | 2.144 |
| ∠(O$_1$ZnN$_4$) | 173.4 | 172.4 |
| ∠(N$_1$ZnN$_2$) | 118.7 | 126.2 |
| ∠(N$_1$ZnN$_3$) | 116.6 | 112.2 |
| ∠(N$_1$ZnN$_4$) | 84.9 | 84.9 |
| ∠(N$_1$ZnO$_1$) | 89.0 | 88.0 |
| ∠(N$_2$ZnN$_3$) | 120.3 | 117.4 |
| ∠(N$_2$ZnN$_4$) | 82.2 | 82.9 |
| ∠(N$_3$ZnN$_4$) | 82.0 | 81.7 |

Experimental Example 6

Determination of Dissociation Constants ($K_d^{OP}$ and $K_d^{TP}$)

MOPS buffer solutions (30 mM, pH 7.2, 0.1 M KCl) containing different amounts of ZnSO$_4$ and 10 mM EGTA were prepared.

The concentration of free Zn$^{2+}$ ([Zn$^{2+}$]$_{free}$) was calculated from $K_{Zn-EGTA}^{app}$, [EGTA]$_{free}$, and [Zn$^{2+}$]$_{total}$ using Equation 1:

$$[Zn^{2+}]_{free} = [Zn^{2+}]_{total}/(\alpha_{Zn} \times K_{Zn-EGTA}^{app} \times [EGTA]_{free}) \quad (1)$$

where $$K_{Zn-EGTA}^{app} = K_{Zn-EGTA}/\alpha_{Zn}\alpha_{EGTA},$$

$$\alpha_{Zn} = 1 + 10^{(pH-pK_1)} + 10^{(2pH-pK_1-pK_2)} + 10^{(3pH-pK_1-pK_2-pK_3)} \ldots,$$

$$\alpha_{EGTA} = 1 + 10^{(pK_1-pH+0.11)} + 10^{(pK_1+pK_2-2pH+0.22)} + 10^{(pK_1+pK_2+pK_3-3pH+0.33)} \ldots,$$

and $$[EGTA]_{free} = [EGTA]_{total} - [Zn^{2+}]_{total}.$$

Therefore, $$K^{app}_{Zn-EGTA} = \frac{K_{Zn-EGTA}(1 + 10^{(pK_{Zn-EGTA}-pH)})}{(1 + 10^{(pH-pK_{Zn})})(1 + 10^{(pK_1-pH)} + 10^{(pK_1+pK_2-2pH)})}$$

Then, the stability constant ($K_{Zn-EGTA}$) of the EGTA–$Zn^{2+}$ complex was obtained by the known method. For EGTA (pH 7.2, 0.1 M KCl, 25° C.), $pK_1$, $pK_2$, $pK_3$ and $\log^{K_{Zn-EGTA}}$ were 9.40, 8.79, 2.70 and 12.6, respectively.

When worked out at an ionic strength of 0.1 M, all protonation constants are corrected upward by 0.11, [EGTA]$_{total}$ is fixed to 10 mM, and [$Zn^{2+}$]$_{total}$ is in the range of 0 to 9.5 mM.

[$Zn^{2+}$]$_{free}$ values calculated for the respective solutions are shown in Table 5.

TABLE 5

| [$Zn^{2+}$]$_{total}$ (mM) | 0.50 | 1.00 | 1.50 | 2.00 | 2.50 | 3.00 | 3.50 | 4.00 | 4.99 | 5.99 | 6.98 | 7.98 | 8.97 | 9.47 |
|---|---|---|---|---|---|---|---|---|---|---|---|---|---|---|
| [$Zn^{2+}$]$_{free}$ (nM) | 0.14 | 0.29 | 0.46 | 0.66 | 0.87 | 1.1 | 1.4 | 1.8 | 2.6 | 3.9 | 6.1 | 10 | 22 | 47 |

Figure 3A:
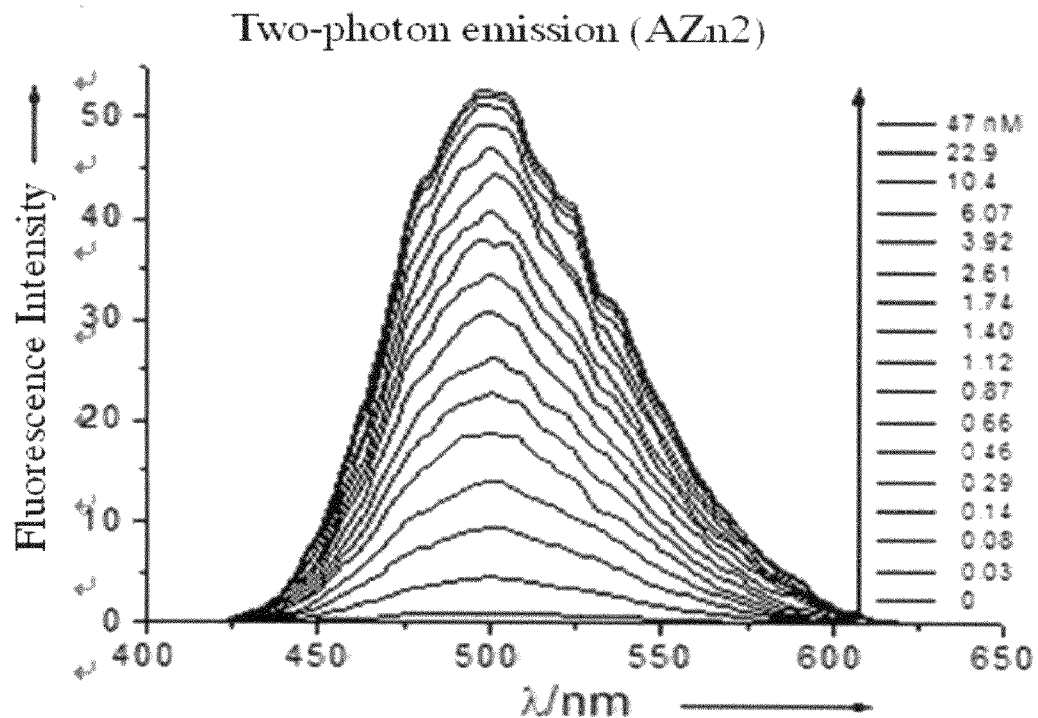
FIGS. 3a through 3f are one-photon absorption and emission spectra and two-photon emission spectra of AZn1 and AZn2 with varying $Zn^{2+}$ concentrations.
Figure 3B:
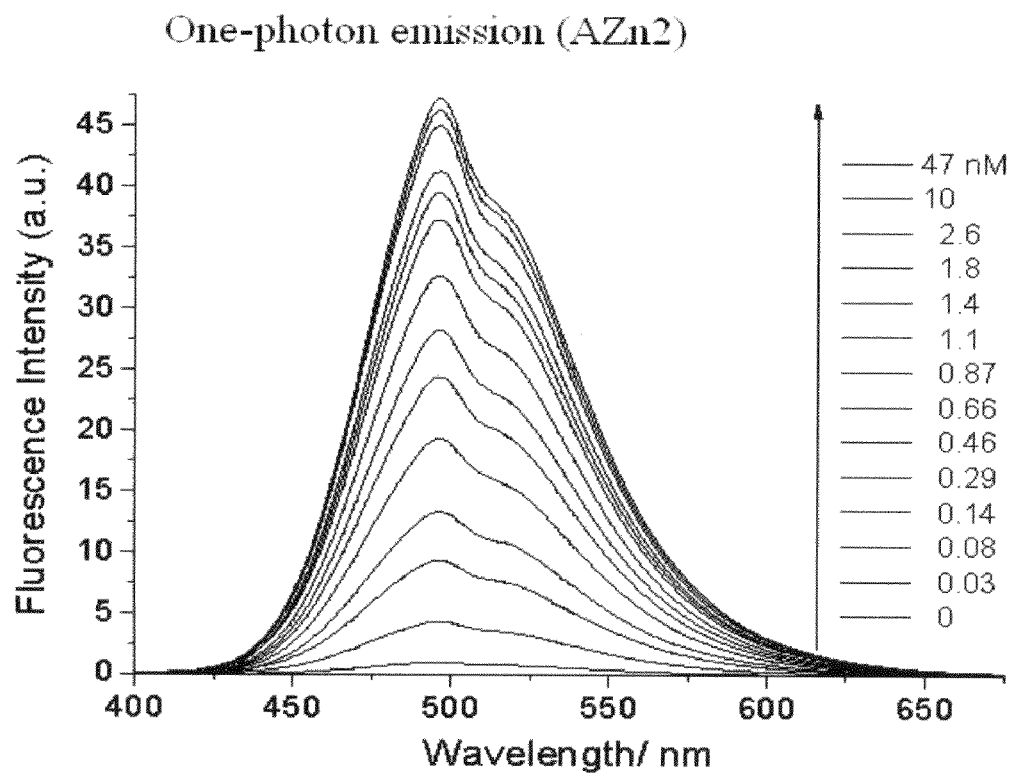
Figure 3C:
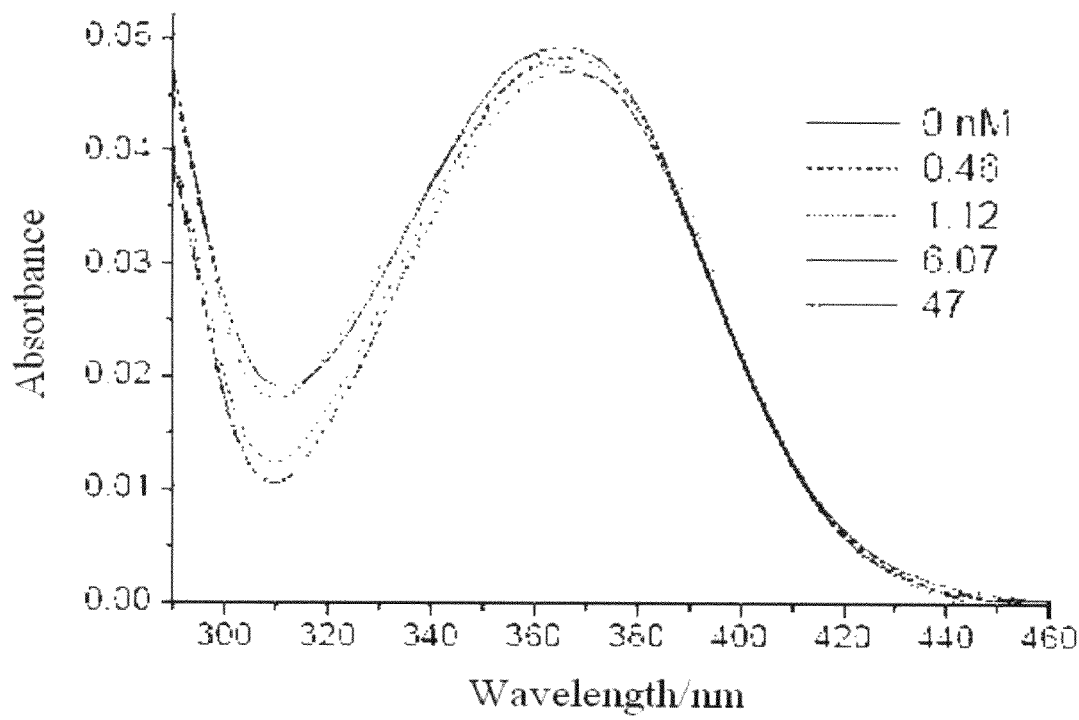
Figure 3D:
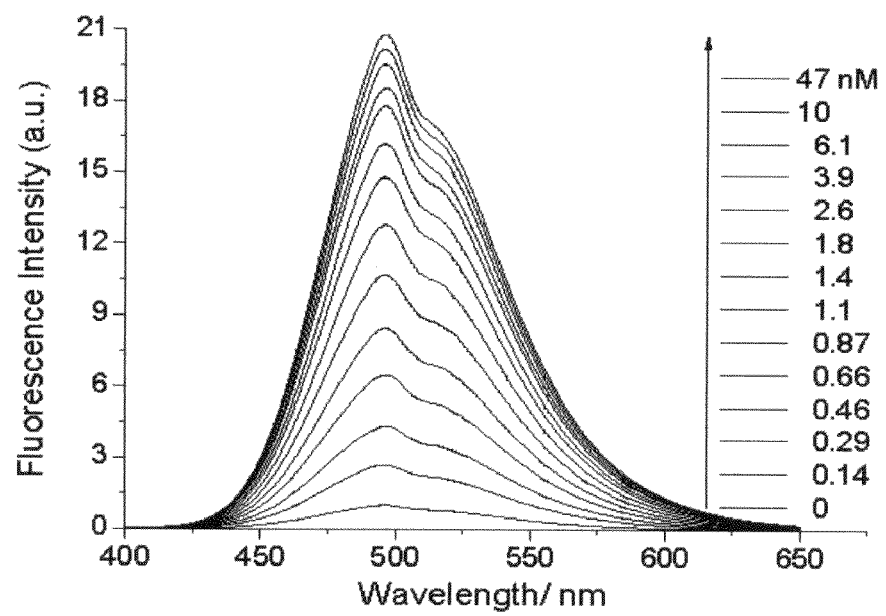
Figure 3E:
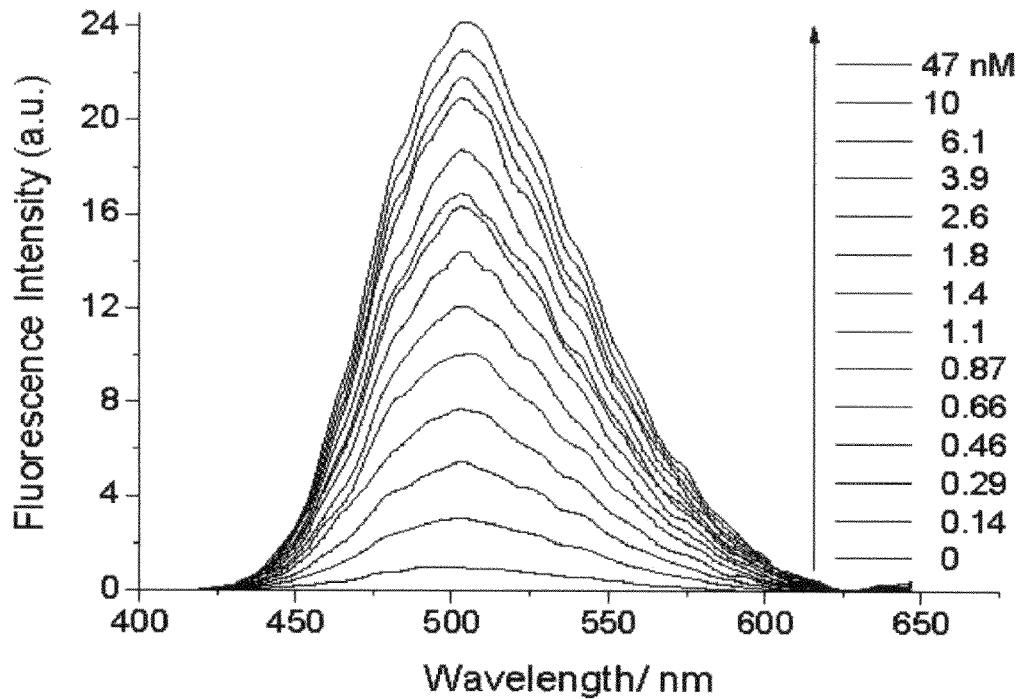
Figure 3F:
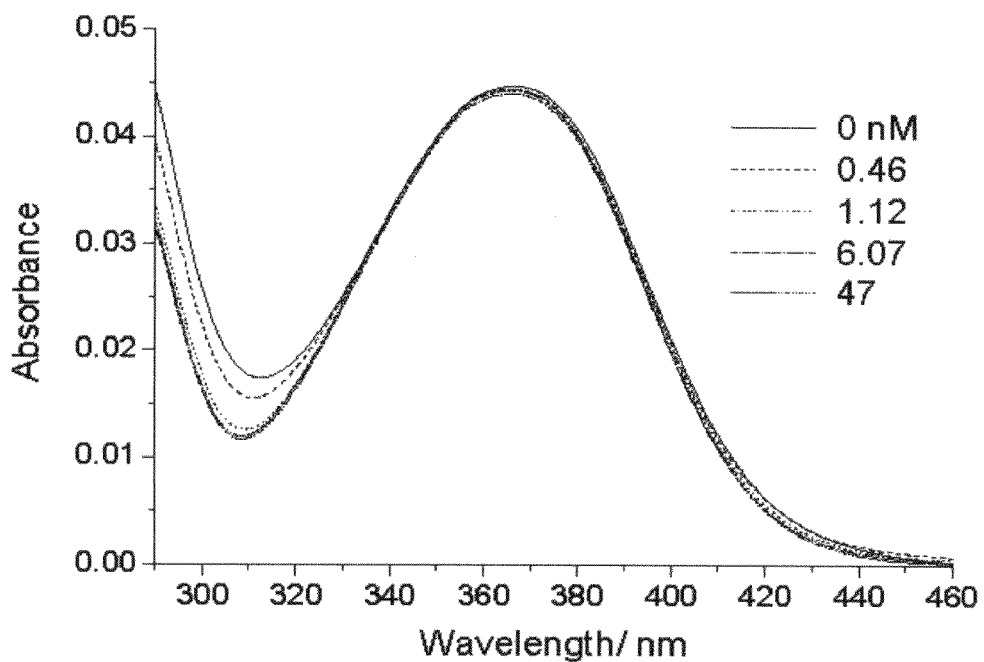

In order to determine accurate dissociation constants for the two-photon probes, fluorescence titration curves were obtained from FIGS. 3a and 3e using Equation 2:

$$F = F_0 + (F_{max} - F_0)\frac{[Zn^{2+}]_{free}}{K_d - [Zn^{2+}]_{free}} \quad (2)$$

where F is the fluorescence intensity, $F_{max}$ is the maximum fluorescence intensity, $F_o$ is the fluorescence intensity in the absence of $Zn^{2+}$, and [$Zn^{2+}$]$_{free}$ is the concentration of free $Zn^{2+}$.

Figure 6A:
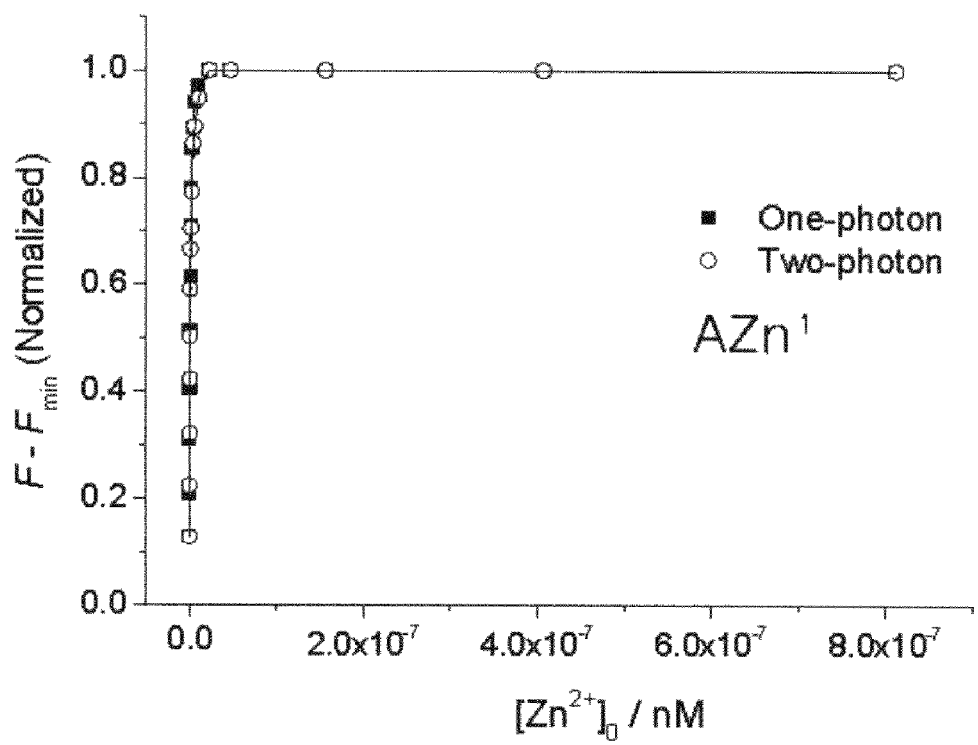
FIGS. 6a and 6b are fluorescence titration curves of AZn1 and AZn2, respectively.
Figure 6B:
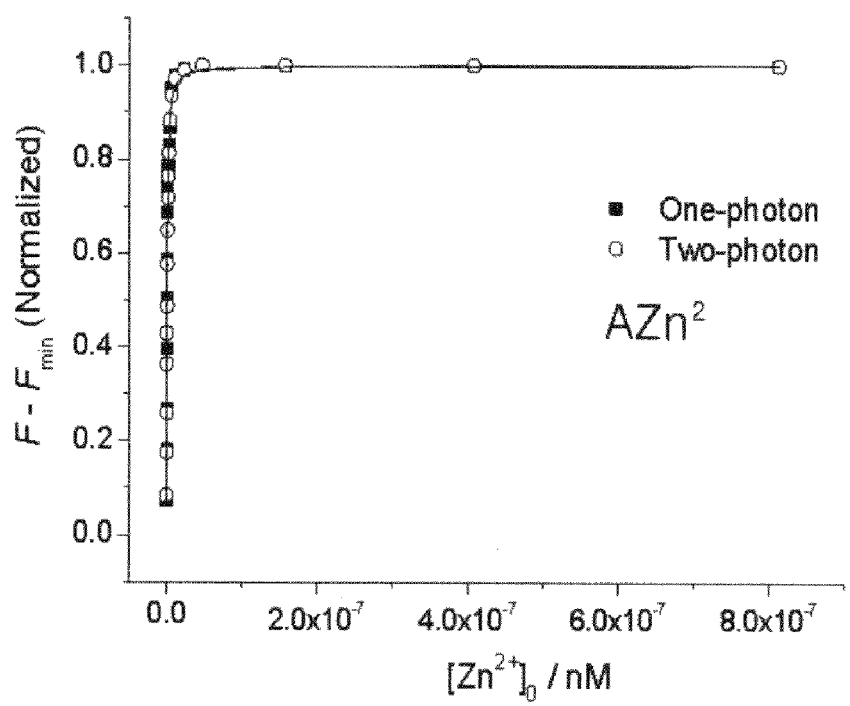

FIGS. 6a and 6b are fluorescence titration curves of the two-photon probes AZn1 and AZn2, respectively.

The $K_d$ value that best fits the titration curve (FIG. 2c) with Equation 2 was calculated by using the Excel program. In order to determine the $K_d^{TP}$ for the two-photon process, the TPEF spectra were obtained with a DM IRE2 Microscope (Leica) excited by a mode-locked titanium-sapphire laser source (Coherent Chameleon, 90 MHz, 200 fs) set at wavelength 780 nm and output power 1,180 mW, which corresponded to approximately 10 mW average power in the focal plane. The TPEF titration curves (FIGS. 3a and 3d) were obtained and fitted to Equation 2 (FIGS. 6a and 6b).

The dissociation constants ($K_d^{OP}$ and $K_d^{TP}$) for AZn1 and AZn2 calculated from the one- and two-photon fluorescence titration curves of FIGS. 6a and 6b are 1.1±0.1 and 0.50±0.04 nM, respectively (Table 2). The detection limits of these probes are in the sub-nM range. It is particularly notable that the $K_d^{TP}$ value for AZn2 is smaller, indicating tighter binding between AZn2 and $Zn^{2+}$, as described above (see Table 3 and FIG. 5).

Experimental Example 7

Evaluation of Probe Selectivity for Metal Cations

Figure 7A:
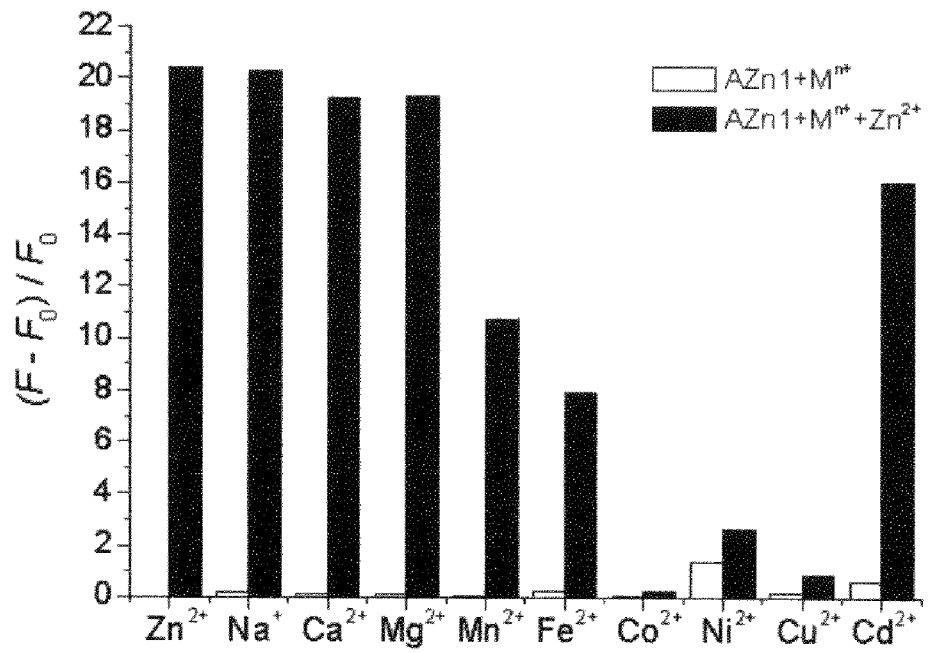
FIGS. 7a and 7b are graphs showing the relative fluorescence intensities of AZn1 and AZn2 (1 μM for each), respectively, after addition of 30 mM MOPS (4-morpholinepropanesulfonic acid) buffer solution (10 mM KCl, 10 mM ethylene glycol-bis(2-aminoethyl ether)-N,N,N',N'-tetraacetic acid (EGTA), pH 7.2); $Na^+$, $Ca^{2+}$ $Mg^{2+}$; $Mn^{2+}$, $Fe^{2+}$, $Co^{2+}$, $Ni^{2+}$, $Cu^{2+}$, $Cd^{2+}$ (10 μM for each); and $Zn^{2+}$ (1 μM)
Figure 7B:
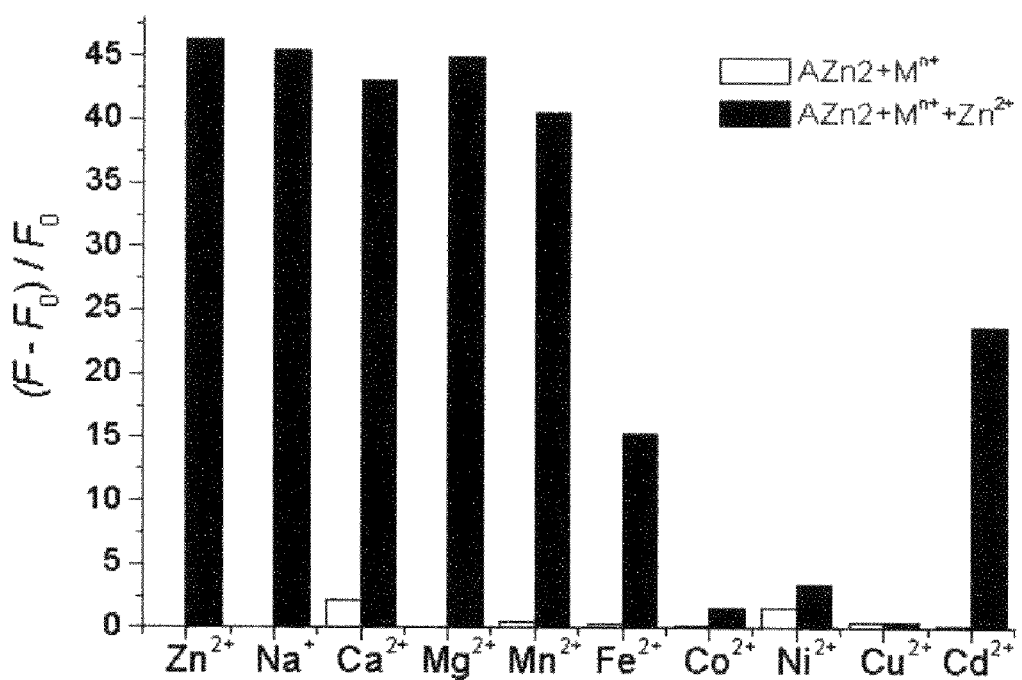

FIGS. 7a and 7b are graphs showing the relative fluorescence intensities of AZn1 and AZn2 (1 μM for each), respectively, after addition of 30 mM MOPS buffer solution (10 mM KCl, 10 mM EGTA, pH 7.2); $Na^+$, $Ca^{2+}$, $Mg^{2+}$; $Mn^{2+}$, $Fe^{2+}$, $Co^{2+}$, $Ni^{2+}$, $Cu^{2+}$, $Cd^{2+}$ (10 μM for each); and $Zn^{2+}$ (1 μM). In the graphs, the filled bars represent the addition of $Zn^{2+}$ and the open bars represent no addition of $Zn^{2+}$.

Referring to FIGS. 7a and 7b, the two-photon probes show high selectivity for $Zn^{2+}$ compared with $Na^+$, $Ca^{2+}$, $Mg^{2+}$, $Mn^{2+}$, $Fe^{2+}$, $Co^{2+}$, $Ni^{2+}$, $Cu^{2+}$, and $Cd^{2+}$.

Figure 8A:
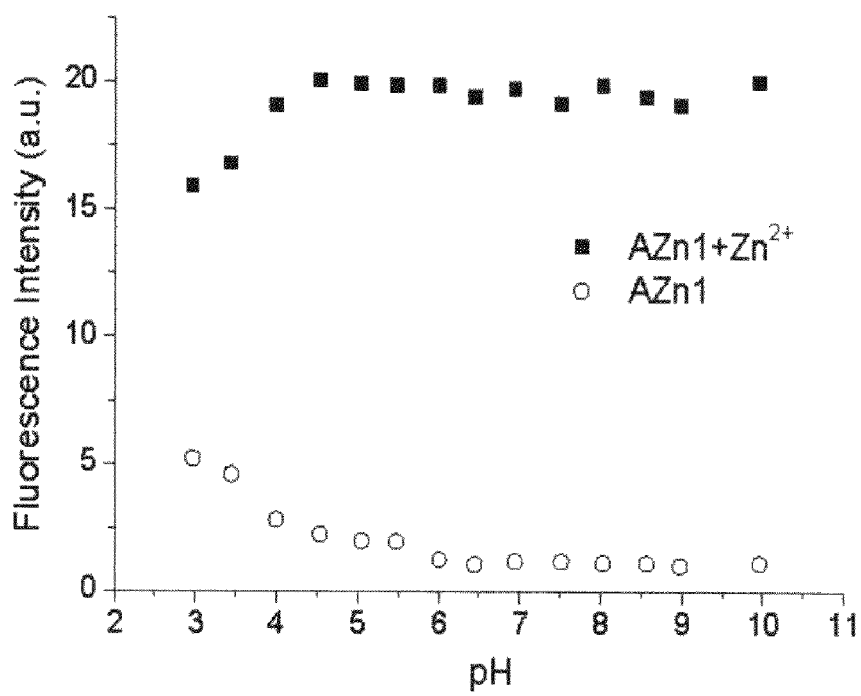
FIGS. 8a and 8b show the one-photon fluorescence intensities of AZn1 and AZn2 (1 μM for each), respectively, as a function of pH when free $Zn^{2+}$ were absent (○) and present at a concentration of 1 μM (■) in mixed solutions of 30 mM MOPS and 100 mM KCl.
Figure 8B:
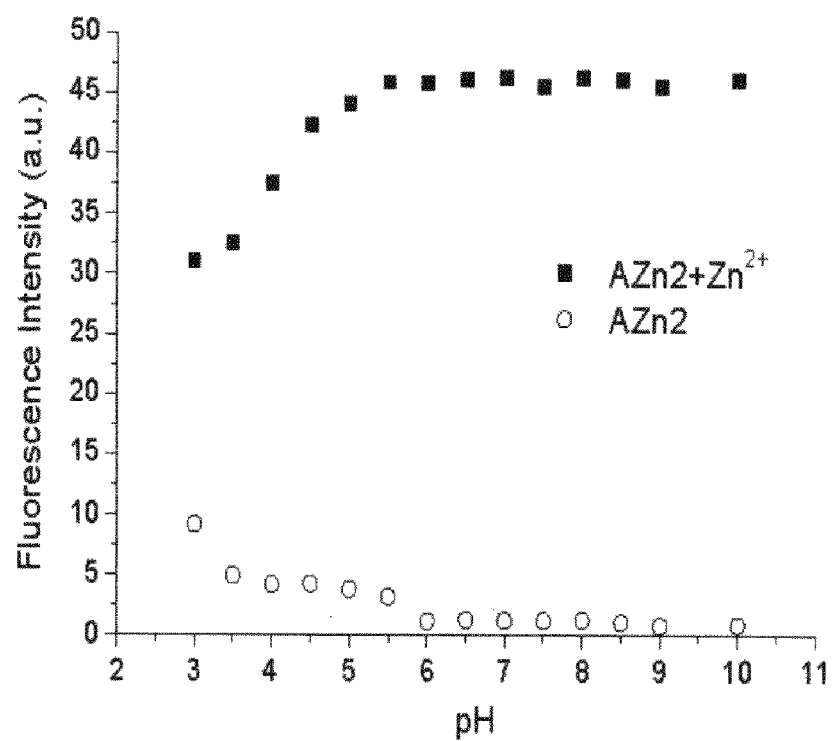

FIGS. 8a and 8b show the one-photon fluorescence intensities of AZn1 and AZn2 (1 μM for each), respectively, as a function of pH when free $Zn^{2+}$ were absent (○) and present at a concentration of 1 μM (■) in mixed solutions of 30 mM MOPS and 100 mM KCl.

Referring to FIGS. 8a and 8b, the two-photon probes AZn1 and AZn2 show high fluorescence intensities in the biologically relevant pH, indicating pH insensitivity.

From the above results, it can be concluded that the two-photon probes show high selectivity for $Zn^{2+}$, are pH-insensitive under biological pH conditions, and are very suitable for the monitoring of intracellular zinc ions.

Experimental Example 8

Measurement of Two-Photon Cross Section and Action Spectra

The two-photon cross section (δ) was determined by using femto second (fs) fluorescence measurement technique.

Specifically, each of the probes AZn1, AZn2, FluZin, and TSQ was dissolved in a 30 mM MOPS buffer (100 mM KCl, 10 mM EGTA, pH 7.2) at a concentration of $5.0 \times 10^{-6}$ M and then the two-photon induced fluorescence intensity was measured at 740-940 nm by using fluorescein as the reference, whose two-photon property has been well characterized. The intensities of the two-photon induced fluorescence spectra of the reference and the sample probe were measured, and the two-photon cross section of the sample probe was calculated according to Equation 3:

$$\delta = \frac{S_s \Phi_r \phi_r c_r}{S_r \Phi_s \phi_s c_s} \delta_r \quad (3)$$

wherein the subscripts s and r represent sample and reference molecules, respectively, δ represents the two-photon cross section, S represents the strength of signals collected by a CCD detector, φ represents the fluorescence quantum efficiency, ϕ represents the total fluorescence collection efficiency of an experimental system, c represents the number density of the molecules within each of the solutions, and $δ_r$ represents the two-photon cross section of reference molecules.

Figure 9:
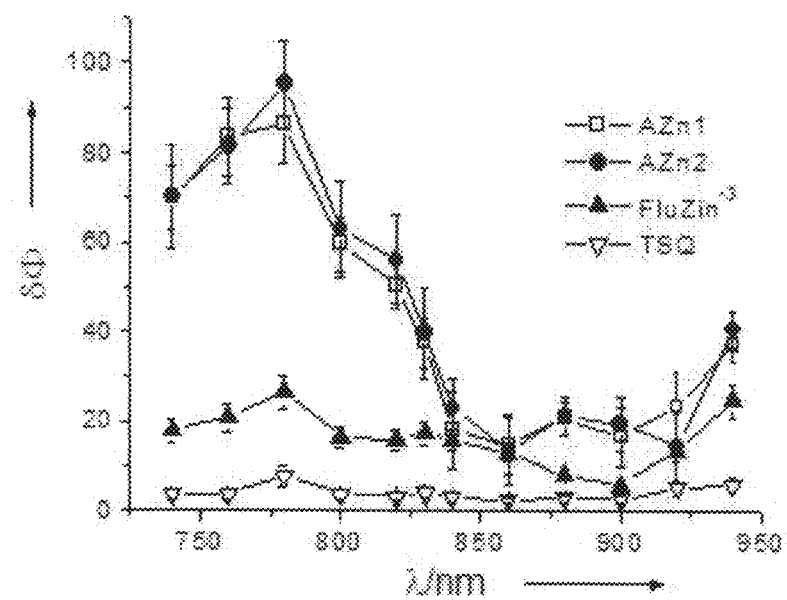
FIG. 9 shows two-photon action spectra of AZn1 (□), AZn2 (●), FluZin (▲) and TSQ (▽) in the presence of 1.8 μM free $Zn^{2+}$.

FIG. 9 shows two-photon action spectra of AZn1 (□), AZn2 (●), FluZin (▲), and TSQ (▽) in the presence of 1.8 μM free $Zn^{2+}$.

Referring to FIG. 9, the two-photon action spectra of the $Zn^{2+}$ complexes with AZn1 and AZn2 in the buffer solutions indicated a ϕδ value of ~90 GM at 780 nm, 4~24-fold larger than those of TSQ and FluZin-3. This indicates that two-photon images for samples stained with AZn1 and AZn2 would be much brighter than those stained with the commercial probes (TSQ and FluZin-3). These results can also be clearly found in Table 2.

Experimental Example 9

Observation of Cells Using the Two-Photon Probes 293 cells were incubated in DMEM (WelGene) supplemented with 10% FBS (WelGene), penicillin (100 unit/ml) and streptomycin (100 μg/ml).

Two days before imaging, the cells were transferred to glass-bottomed dishes (MatTek) and plated thereon. For labeling, the growth medium was replaced with FBS-free DMEM. The cells were incubated under 5% $CO_2$, 37° C., using a 2 μM sensor for 30 minutes, washed three times with phosphate-buffered saline (PBS; Gibco), and further incubated in a colorless serum-free medium. Meanwhile, primary cortical cultures were taken from cerebral cortices of 1-day-old rats (Sprague-Dawley (SD)). The cerebral cortices were dissociated in Hank's balanced salt solution (HBSS; Gibco BRL, Gaithersburg, Md., USA) containing 1 U/ml papain (Worthington Biochemical Corporation, NJ, USA), plated at a density of 100 to 200 cells/mm² on poly-D-lysine and laminin-coated glass cover slips, and maintained in Neurobasal media (Gibco) supplemented with 2% B-27 (Gibco) and penicillin/streptomycin in a $CO_2$ incubator at 37° C. After storage in test tubes for 7-15 days, the cortical cultures were washed three times with PBS and incubated in the presence of AZn2 (2 μM) in PBS at 37° C. for 30 minutes.

Two-photon fluorescence microscopy images of cells and tissue labeled with AZn2 were obtained with spectral confocal and multiphoton microscopes (Leica TCS SP2) with a ×100 oil objective and numerical aperture (NA)=1.30. The two-photon fluorescence microscopy images were obtained by exciting the two-photon probe with a mode-locked titanium-sapphire laser source (Coherent Chameleon, 90 MHz, 200 fs) set at wavelength of 780 nm and an output power of 1,230 mW, which corresponded to approximately 10 mW average power in the focal plane. To obtain images at 360-460 nm and 500-620 nm range, internal PMTs were used to collect the signals in an 8 bit unsigned 512×512 pixels at 400 Hz scan speed.

Figure 10:
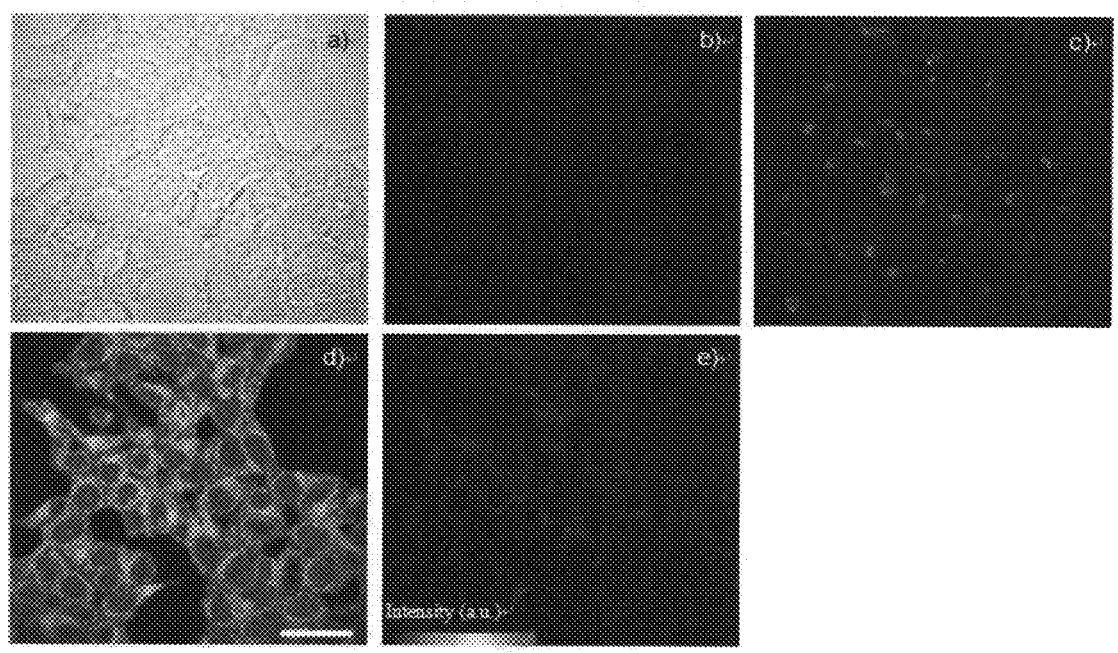
FIG. 10 shows two-photon microscopy (TPM) images of AZn2 (2 μM)-labeled 293 cells.

FIG. 10 shows two-photon microscopy (TPM) images of the AZn2 (2 μM)-labeled 293 cells: (a) is a bright field image, (b) is an image of the labeled cells collected at 360-460 nm before addition of 10 mM S-nitrosocysteine (SNOC) to the imaging solution, (c) is an image of the labeled cells collected at 500-620 nm before addition of 10 mM SNOC to the imaging solution, (d) is an image of the labeled cells collected at 360-460 nm after addition of 10 mM SNOC to the imaging solution, and (e) is an image of the labeled cells collected at 500-620 nm after addition of 10 mM SNOC to the imaging solution.

Figure 11:
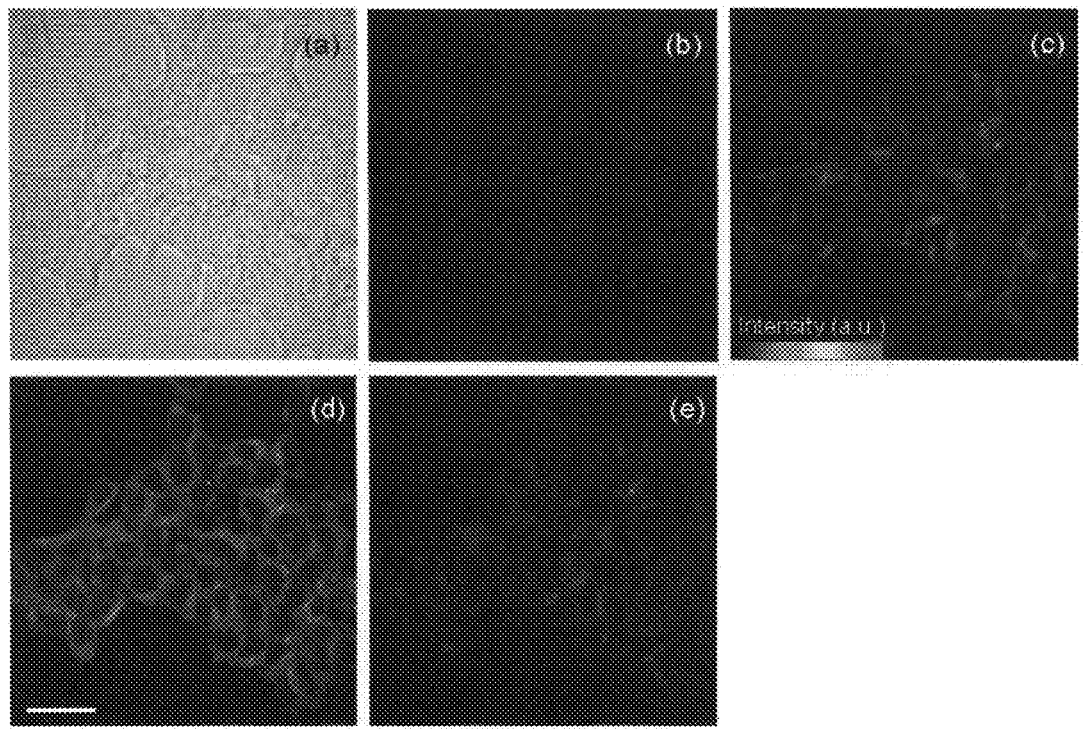
FIG. 11 shows TPM images of AZn1 (2 μM)-labeled 293 cells.

FIG. 11 shows TPM images of AZn1 (2 μM)-labeled 293 cells: (a) is a bright field image, (b) is an image of the labeled cells collected at 360-460 nm before addition of 10 mM SNOC to the imaging solution, (c) is an image of the labeled cells collected at 500-620 nm before addition of 10 mM SNOC to the imaging solution, (d) is an image of the labeled cells collected at 360-460 nm after addition of 10 mM SNOC to the imaging solution, and (e) is an image of the labeled cells collected at 500-620 nm after addition of 10 mM SNOC to the imaging solution.

The TPM images of 293 cells labeled with the two-photon probes AZn1 and AZn2 emitted no TPEF at 360-460 nm (see (b) of FIGS. 10 and 11), and appreciable TPEF at 500-620 nm (see (c) of FIGS. 10 and 11).

For comparison, the TPM images of the cells labeled with Acedan-derived TP probes for $Mg^{2+}$ (AMg1) and $Ca^{2+}$ (ACa1) emitted TPEF at 500-620 and 360-460 nm regions, which had been attributed to the probes associated with cytosol and membrane, respectively (H. M. Kim, B. R. Kim, J. H. Hong, J.-S. Park, K. J. Lee, B. R. Cho, *Angew. Chem.* 2007, 119, 7589-7592; *Angew. Chem. Int. Ed.* 2007, 46, 7445-7448).

Hence, AZn2 appears to be predominantly located in the cytosolic compartments, probably due to the lower molecular weight (Mw), and thereby can detect $[Zn^{2+}]_i$ in live cells without interference from the membrane-bound probes. Moreover, because the fluorescence intensities of the two-photon probes increase slightly at pH<4 (FIGS. 8a and 8b), there is a possibility that the probes in the acidic vesicles might partially contribute to the TPM images. To rule out such possibility, 293 cells and primary cortical cultures were co-stained with AZn2 and LysoTracker Red (LTR), a well known one-photon fluorescent probe for the acidic vesicles, and the images were co-localized. The results are shown in FIGS. 12 and 13.

Figure 12:
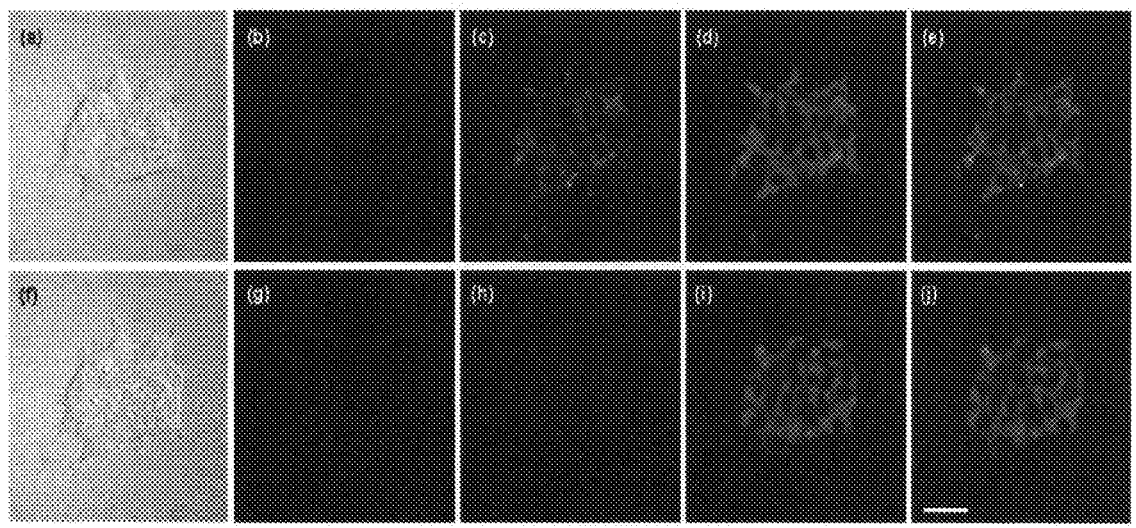
FIG. 12 shows TPM images of AZn2- and LTR (2 μM for each)-labeled 293 cells.

FIG. 12 shows images of AZn2- and LTR (2 μM for each)-labeled 293 cells: (a)-(e) and (f)-(j) are images of the labeled cells before and after addition of 100 μM N,N,N',N'-tetrakis (2-pyridyl)ethylenediamine) (TPEN) to the imaging solution, respectively. More specifically, (a) and (f) are bright field images, (b) and (g) are pseudo colored images of the AZn2-labeled 293 cells collected at 360-460 nm, (c) and (h) are pseudo colored images of the AZn2-labeled 293 cells collected at 500-580 nm, (d) and (i) are OPM images of the LTR-labeled 293 cells collected at 600-650 nm, and (e) and (j) are co-localized images. The one-photon and two-photon excitations were performed at 543 nm and 780 nm, respectively, the scale bar is 30 μm, and the images shown are representative images from replicate experiments (n=5).

Figure 13:
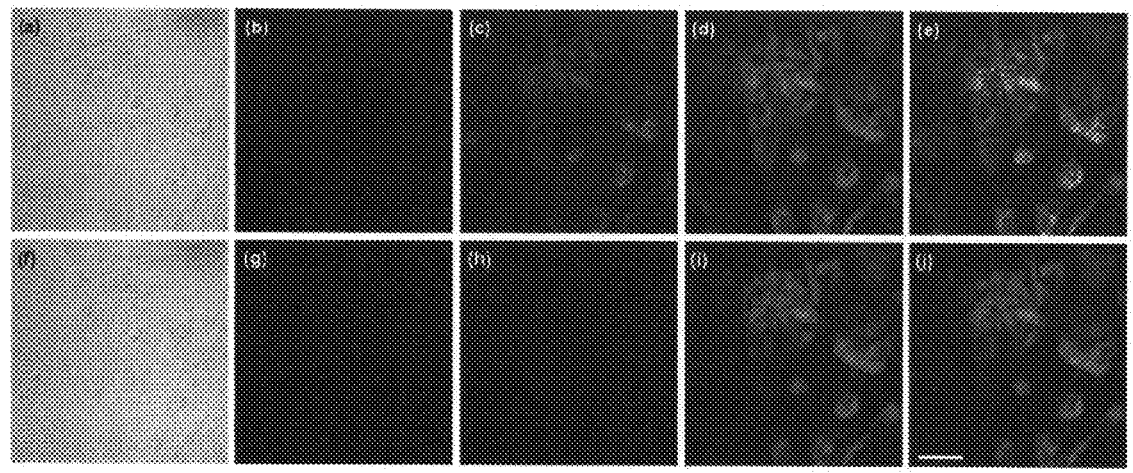
FIG. 13 shows TPM images of AZn1- and LTR (2 μM for each)-labeled 293 cells.

FIG. 13 is images of AZn1- and LTR (2 μM for each)-labeled 293 cells: (a)-(e) and (f)-(j) are images of the labeled cells before and after addition of 100 μM TPEN to the imaging solution, respectively. More specifically, (a) and (f) are bright field images; (b) and (g) are pseudo colored images of the AZn1-labeled 293 cells collected at 360-460 nm; (c) and (h) are pseudo colored images of the AZn1-labeled 293 cells collected at 500-580 nm; (d) and (i) are OPM images of the LTR-labeled 293 cells collected at 600-650 nm; and (e) and (j) are co-localized images. The one-photon and two-photon excitations were performed at 543 nm and 780 nm, respectively, the scale bar is 30 μm, and the images shown are representative images from replicate experiments (n=5).

Referring to FIGS. 12 and 13, the co-localized images did not merge. Moreover, the TPM images taken after treatment with 100 μM TPEN, a membrane permeable $Zn^{2+}$ chelator that can effectively remove $Zn^{2+}$, emitted little TPEF, and the OPM images taken before and after treatment with TPEN are nearly identical ((d) and (i) of FIGS. 12 and 13). Hence, the two-photon probes can selectively detect $[Zn^{2+}]_i$ in neurons by TPM without interference from the probes associated with the acidic vesicles.

Experimental Example 10

Two-Photon Excitation Fluorescence (TPEF) Analysis

Figure 14:
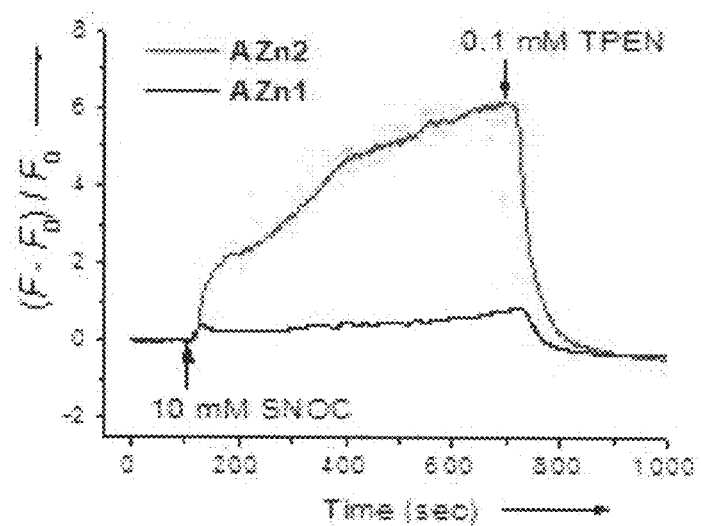
FIG. 14 shows two-photon excitation fluorescence (TPEF) spectra of AZn1- and AZn2-labeled 293 cells after addition of 10 mM S-nitrosocysteine (SNOC)

To demonstrate the utility of the two-photon probes in the cell imaging, TPEF of the AZn2-labeled 293 cells was monitored after addition of 10 mM SNOC, an endogenous NO donor that triggers the release of $Zn^{2+}$, and the results are shown in FIG. 14.

Referring to FIG. 14, the TPEF intensity increased gradually with time and then decreased abruptly upon addition of 0.1 mM TPEN, a membrane permeable Zn²⁺ chelator that can effectively remove Zn²⁺. A similar result was observed for the two-photon probe AZn1 except that the response was smaller, due to the larger $K_d$. Hence, the two-photon probes are clearly capable of detecting the $[Zn^{2+}]_i$ in live cells for longer than 1,000 seconds.

Experimental Example 11

Monitoring of $Zn^{2+}$ in Rat Hippocampal Slice

To demonstrate the utility of the two-photon probes in deep tissue imaging, a rat hippocampal slice was monitored. In this experimental example, TPM images were obtained from a part of acute rat hippocampal slice incubated with 10 µM AZn2 for 30 min at 37° C. Because the slice of a 14-day old rat was too big to show with one image, several TPM images were obtained in the same plane at ~120 µm depth and combined.

Figure 15:
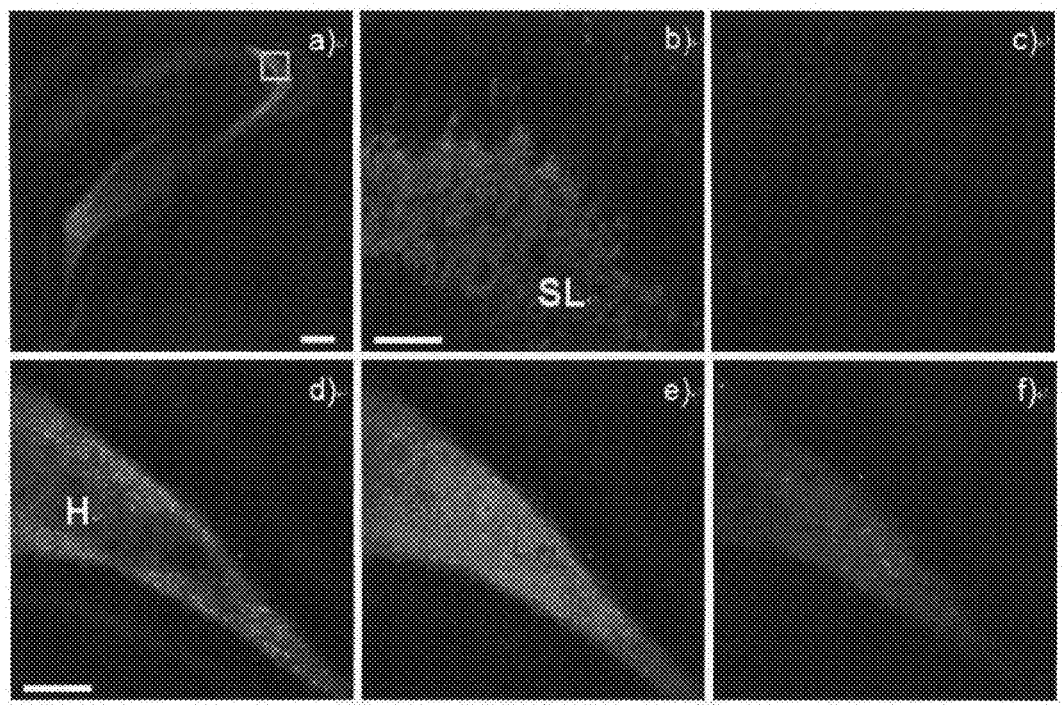
FIG. 15 shows TPM images of a rat hippocampal slice stained with 10 μM AZn2.

The TPM images are shown in FIG. 15: (a) is the TPM image obtained at a depth of ~120 µm with magnification 10×; (b) and (c) are the TPM images with magnification 100× in the stratum lucidum of CA3 regions before and after addition of 200 µM TPEN, respectively; and (d) through (f) are the TPM images in the hilus of dentate gyrus regions at a depth of ~100 µm (d) before and (e) after addition of 50 mM KCl to the imaging solution and (f) after addition of 200 µM TPEN to (e).

The image (a) reveals intense fluorescence in the stratum lucidum of CA3 and the hilus of dentate gyrus (yellow box of (a)). The image (b) obtained at a higher magnification clearly shows that $[Zn^{2+}]_i$ is concentrated in the mossy fiber axon terminals of pyramidal neurons in the CA3 region. The negligible TPEF (c) after addition of TPEN, which effectively remove the $[Zn^{2+}]_i$, provides a supporting evidence for this observation.

Figure 16:
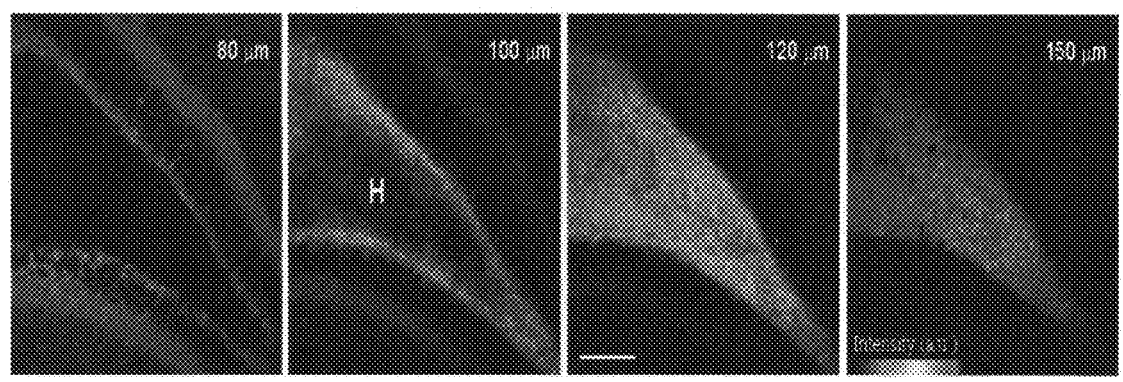
FIG. 16 shows TPM images of the hilus of dentate gyrus of a rat hippocampal slice stained with AZn2 (10 μM)

FIG. 16 shows TPM images (magnification 20×) of the hilus of dentate gyrus of a rat hippocampal slice stained with AZn2 (10 µM) at different depths.

Figure 17:
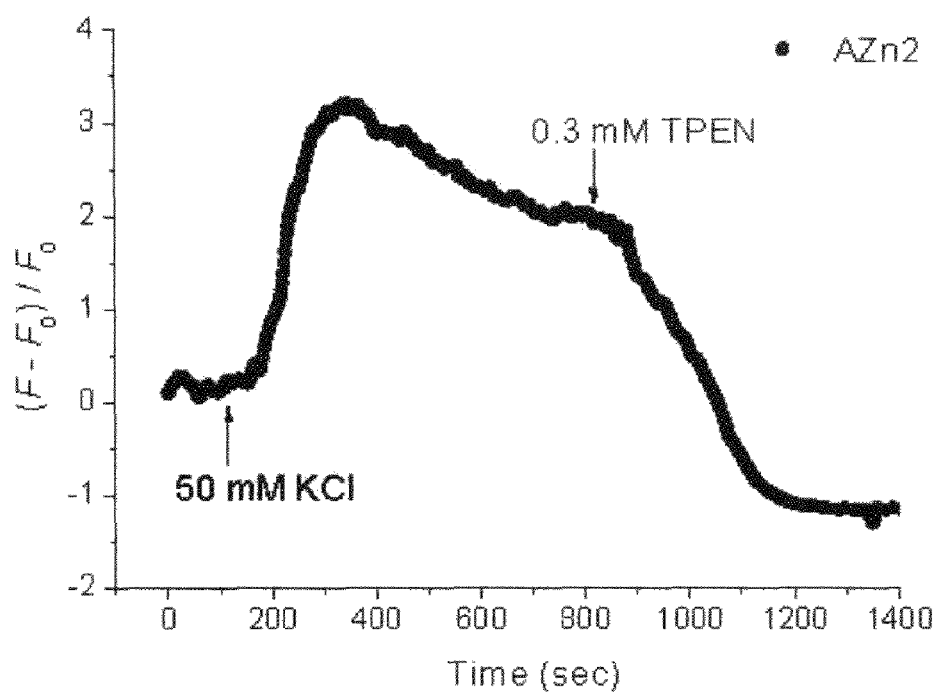
FIG. 17 is a graph showing the relative TPEF intensities of AZn2 in the hilus of dentate gyrus of a rat hippocampal slice.

Referring to FIG. 16, the TPM images obtained at 80-150 µm depth revealed the $[Zn^{2+}]_i$ distribution in the mossy fibers of dentate granule neurons near the hilus exclusively the given plane along the z direction (i.e. thickness). When 50 mM KCl, a membrane depolarizer causing the release of $Zn^{2+}$, was added to the imaging solution, the TPEF intensity increased, and then decreased upon treatment with TPEN. Similar results can also be found in (d)-(f) of FIG. 15. FIG. 17 shows the relative TPEF intensities of AZn2 in the hilus of dentate gyrus of the rat hippocampal slice. A clear reduction in TPEF due to the addition of TPEN is observed in FIG. 17.

These findings demonstrate that the two-photon probes are very effectively capable of detecting intracellular free $Zn^{2+}$ at 80-150 µm depth in live tissues.

In conclusion, the two-photon probes show 24~52-fold TPEF enhancement in response to $Zn^{2+}$ and dissociation constants ($K_d^{TP}$) of 1.1±0.1 and 0.50±0.04 nM, respectively. In addition, the two-photon probes are pH-insensitive in the biological relevant pH and emit 4~24-fold stronger TPEF than TSQ and FluZin-3 as conventional two-photon probes for the detection of $Zn^{2+}$. Better than currently available two-photon probes, the two-photon probes can selectively detect intracellular free $Zn^{2+}$ for longer than 1,000 seconds. Furthermore, the two-photon probes can very effectively image and monitor intracellular free $Zn^{2+}$ without interference or disturbance from membrane-bound two-photon probes and other metal ion species.

What is claimed is:

1. A two-photon probe for real-time monitoring of intracellular free zinc ions, represented by Formula 1:

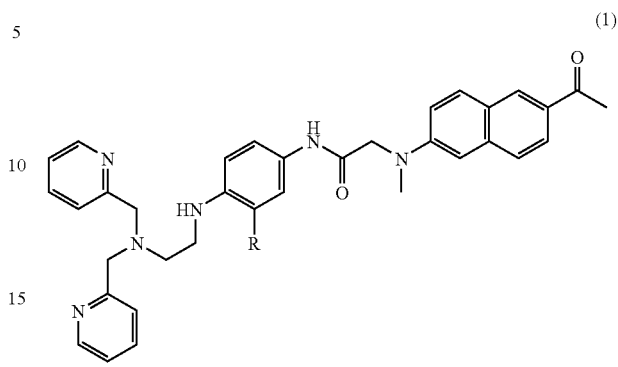

(1)

wherein R is H or OCH₃.

2. A method for preparing a two-photon probe for real-time monitoring of intracellular free zinc ions, represented by Formula 1:

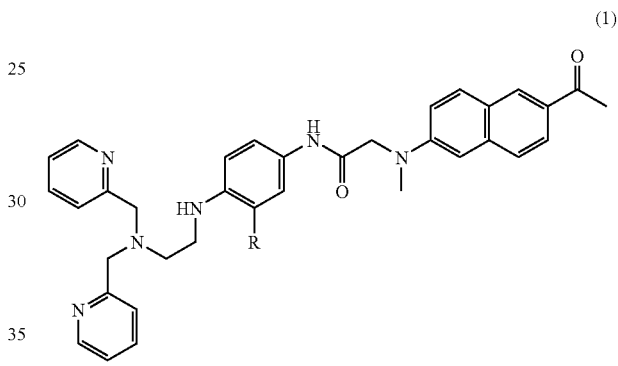

(1)

wherein R is H or OCH₃,
the method comprising (a) adding the compound of Formula 2:

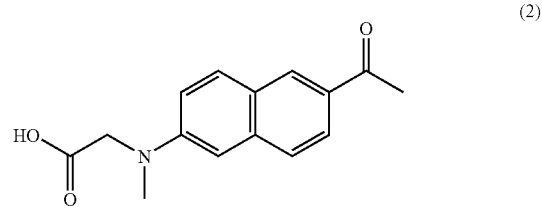

(2)

to an organic solvent and stirring the mixture, and (b) reacting the compound of Formula 2 with the compound of Formula 3:

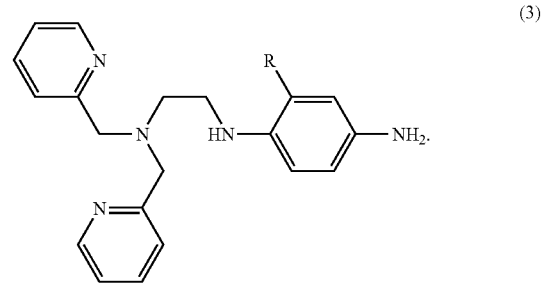

(3)

wherein R is H or OCH$_3$,
by contacting the mixture of step (a) with the compound of formula 3 to form a reaction product.

3. The method of claim 2, further comprising isolating the compound of Formula 1 from the reaction product after step (b).

4. The method of claim 2, wherein the organic solvent is selected from 1-hydroxybenzotriazole, 1,3-dicyclohexylcarbodiimide and a mixture thereof.

5. The method of claim 3, wherein the compound of Formula 1 is isolated by extraction.

6. A method for real-time monitoring of intracellular free zinc ions, the method comprising injecting the two-photon probe of claim 1 into cells of interest and observing two-photon excitation fluorescence (TPEF) images of the cells.

7. The method of claim 6, wherein the TPEF images are obtained from the cells at a depth of 80 to 150 μm in live tissues.

8. The method of claim 6, wherein the TPEF images are observed for longer than 1,000 seconds.

* * * * *